United States Patent [19]

Glucksmann

[11] Patent Number: 5,795,726
[45] Date of Patent: Aug. 18, 1998

[54] METHODS FOR IDENTIFYING COMPOUNDS USEFUL IN TREATING TYPE II DIABETES

[75] Inventor: M. Alexandra Glucksmann, Somerville, Mass.

[73] Assignee: Millennium Pharmaceuticals, Inc., Cambridge, Mass.

[21] Appl. No.: 782,047

[22] Filed: Jan. 10, 1997

Related U.S. Application Data

[63] Continuation-in-part of Ser. No. 760,246, Dec. 4, 1996, which is a continuation-in-part of Ser. No. 749,431, Nov. 15, 1996, which is a continuation-in-part of Ser. No. 748,229, Nov. 12, 1996, abandoned.

[51] Int. Cl.$^6$ .............................. C12Q 1/02; C12Q 1/66; C12Q 1/68; C07H 21/04
[52] U.S. Cl. .................... 435/7.21; 435/4; 435/6; 435/8; 536/23.5
[58] Field of Search ................ 435/4, 6, 8, 7.21; 536/23.5

[56] References Cited

FOREIGN PATENT DOCUMENTS

WO 92/11365  7/1992  WIPO .
WO 94/00558  1/1994  WIPO .

OTHER PUBLICATIONS

Byrne, Maria M. et al., "Altered Insulin Secretory Responses to Glucose in Diabetic and Nondiabetic Subjects with Mutations in the Diabetes Susceptibility Gene MODY3 on Chromosome 12", *Diabetes* 45:1503–1510, Nov. 1996.

Fajans, Stefan S. et al., "Maturity–Onset Diabetes of the Young", *Life Sciences*, 6(55):413–422, 1994.

Vaxillaire, Martine et al., "A Gene for Maturity Onset Diabetes of the Young (MODY) Maps to Chromosome 12q", *Natural Genetics* 9:418–423, Apr. 1995.

Zhong, Weimin et al., "Tissue–Specific Regulation of Mouse Hepatocyte Nuclear Factor 4 Expression", *Molecular and Cellular Biology* 11(14):7276–7284, Nov. 1994.

Barrera–Hernandez, Gonzalo et al., "Effects of Diabetes Mellitus on Hepatocyte Nuclear Factor 1 Decrease Albumin Gene Transcription", *The Journal of Biological Chemistry*, 17(271):9969–9975, Apr. 1996.

Bach, Ingolf and Yaniv, Moshe "More Potent Transcriptional Activators or a Transdominant Inhibitor of the HNF1 Homeoprotein Family are Generated by Alternative RNA Processing", *The EMBO Journal*, 11(12)4229–4242 (and corrigendum), 1993.

Ringeisen, François, et al., "The Transactivation Potential of Variant Hepatocyte Nuclear Factor 1 is Modified by Alternative Splicing", *The Journal of Biological Chemistry* 34(268):25706–25711, 1992.

Stoffel, Markus et al. "A Yeast Artificial Chromosome–Based Map of the Region of Chromosome 20 Containing the Diabetes–Susceptibility Gene, MODY1, and a Myeloid Leukemia Related Gene", *Proc. Natl. Acad. Sci., USA* 93:3937–3941, 1996.

Bryne, Maria M. et al., "Altered Insulin Secretory Responses to Glucose in Subjects with a Mutation in the MODY1 Gene on Chromosome 20", *Diabetes* 44:699–704, 1995.

Vaxillaire, Martine et al., "Search for a Third Susceptibility Gene for Maturity–Onset Diabetes of the Young", *Diabetes* 43:389–395, 1994.

Drewes, Thorsten et al. "Human Hepatocyte Nuclear Factor 4 Isoforms are Encoded by Distinct and Differentially Expressed Genes" *Molecular and Cellular Biology* 3(16):925–931, 1996.

Beck–Nielsen, Henning et al., "Insulin Action and Insulin Secretion in Identical Twins with MODY", *Diabetes* 37:730–735, 1988.

Lesage, Suzanne, et al. "Linkage Analyses of the MODY3 Locus on Chromosome 12q with Late–Onset NIDDM", *Diabetes* 44:1243–1247, 1995.

*Primary Examiner*—David Saunders
*Assistant Examiner*—F. Pierre VanderVegt
*Attorney, Agent, or Firm*—Beth E. Arnold, Esq.; Foley, Hoag & Eliot LLP

[57] ABSTRACT

Methods for identifying compounds, which modulate the bioactivity of human hepatic nuclear factor-1 (HNF-1), and which are therefore useful in treating type II diabetes are disclosed.

10 Claims, 5 Drawing Sheets

METHODS FOR IDENTIFYING COMPOUNDS USEFUL IN TREATING TYPE II DIABETES

RELATED PATENT APPLICATIONS

The patent application is a continuation-in-part (CIP) application of U.S. Ser. No. 08/760,246 filed Dec. 4, 1996, which itself is a CIP of U.S. Ser. No. 08/749,431 filed Nov. 15, 1996 which itself is a continuation-in-part of U.S. Ser. No. 08/748,229 filed Nov. 2, 1996 (abandoned).

1. BACKGROUND OF THE INVENTION

Diabetes mellitus is among the most common of all metabolic disorders, affecting up to 11% of the population by age 70. Type I diabetes (insulin dependent diabetes mellitus or IDDM) represents about 5 to 10% of this group and is the result of a progressive autoimmune destruction of the pancreatic β-cells with subsequent insulin deficiency.

There are two classes of type II diabetes (non-insulin dependent diabetes mellitus or NIDDM). One typically presents in older people; thus it is sometimes called mature onset diabetes. Another form, though similar to mature onset, presents in a subject at a very early age. Type II diabetes represents 90–95% of the affected population, more than 100 million people worldwide (King, H. and Zimmer, P. (1988) *Wld Hlth. Statist. Quart.* 41:190–196; Harris, M. I., et al. (1992) *Diabetes Care* 15:815–819), and is associated with peripheral insulin resistance, elevated hepatic glucose production, and inappropriate insulin secretion (DeFronzo, R. A. (1988) *Diabetes* 37:667–687). Family studies point to a major genetic component (Newman, B. et al. (1987) *Diabetologia* 30:763–768; Köbberling, J. (1971) *Diabetologia* 7:46–49; Cook, J. T. E. (1994) *Diabetologia* 37:1231–1240). However, few susceptibility genes have been identified.

Certain loci have been linked to rare early-onset forms of Type II diabetes that is associated with chronic hyperglycemia and monogenic inheritance (i.e. maturity onset diabetes of the young (MODY) loci) (Bell, G. I. et al. (1991) *Proc. Natl. Acad. Sci. USA* 88:1484–1488; Froguel, P. et al. (1992) *Nature* 356:162–164; Hattersley, A. T. et al. (1992) *Lancet* 339:1307–1310; Vaxillaire, M. et al. (1995) *Nature Genet.* 9:418–423. The defects in the glucokinase (GCK) gene on human chromosome 7 have been found to be responsible for the relatively rare MODY (MODY2) (Froguel, P. et al. (1992) *Nature*, 356:162–164).

Linkage studies have shown that a different gene associated with MODY is tightly linked to the adenosine deaminase gene (ADA) on human chromosome 20q. This as yet unidentified gene is referred to as MODY1. (Bell, G. I. et al., (1991) *Proc. Natl. Acad. Sci. USA*, 88:1484–1488; Cox, N. J. et al., (1992) *Diabetes*, 41:401–407; Bowden, D. W. et al., (1992), *Diabetes*, 41:88–92). The MODY1 locus has since been refined to a 13 centimorgan interval (about 7 Mb) on chromosome 20 in bands q11.2–q13.1 (Rothschild, C. B. et al., (1992) *Genomics* 13:560–564). A yeast artificial chromosome-based map of the region has been made (Stoffel, M. et al., (1996) *Proc. Natl. Acad. Sci. USA* 93:3937–3941). A number of studies have failed to find linkage of NIDDM with the MODY1 region (Baroni, M. G. et al., (1992) *Diabetes* 41:1640–1643; Dow, E et al., (1994) *Diabet. Med.* 11:856–861; Chuang, L. M. et al., (1995) *Diabetolgia* 38:1490–1491).

Linkage studies have also shown that yet a further gene responsible for MODY is contained within a 7 centimorgan interval bracketed by D12586 and D12S342 on human chromosome 12q. This as yet unidentified gene is referred to as MODY3. (Vaxillaire, M. et al., (1995) *Nature Genetics*, 9:418–423). One study reports that this locus is not implicated in certain late-onset NIDDM (Lesage, S. et al., (1995) *Diabetes*, 44:1243–1247).

Another locus has been identified for a rare early-onset form of type II diabetes with mitochondrial inheritance (Van den Ouwenland, J. M. W. et al., (1992) *Nature Genet.* 1:368–371). In addition, Harris et al. (Harris, C. L. et al. (1996) *Nature Genet.* 13:161–166) have identified a type II diabetes linked locus on chromosome 2, referred to as NIDDM1, that appears to play a role in Mexican American diabetes. Further, Mahtani et al., (Mahtani, M. M. et al. (1996) *Nature Genetics* 14:90–94) report evidence of the existence of a gene on human chromosome 12, referred to as NIDDM2, that causes NIDDM associated with low insulin secretion.

Effective therapies for type II diabetes are needed.

2. SUMMARY OF THE INVENTION

In one aspect, the invention features methods for treating diabetes. In a preferred embodiment, the methods feature administering to a diabetic subject, a therapeutically effective amount of a pharmaceutical composition that modulates the expression of a gene or the activity of a gene product involved in diabetes.

In another aspect, the invention features compounds that modulate the expression of a gene or the activity of a gene product involved in diabetes. In a preferred embodiment, the gene or gene product is a hepatic nuclear factor (HNF) gene or protein. In another preferred embodiment, the gene or gene product is a gene or gene product that is up-or down-regulated by an HNF gene or protein. In yet a further preferred embodiment, the gene contains an HNF binding site in its promoter region or the gene product is encoded by a gene that contains an HNF binding site in its promoter region. Pharmaceutical compositions that modulate the expression of a gene or the activity of a gene product involved in diabetes can be comprised of proteins, peptides, peptidomimetics, other small molecules (e.g., carbohydrates, lipids, or other organic molecules) or nucleic acids (e.g. gene replacement therapies, antisense, ribozyme and triplex nucleic acid constructs).

In a preferred embodiment, the pharmaceutical composition is comprised of an agonist of a normal (functional) HNF bioactivity or of a normal (functional) bioactivity encoded by a gene that is up-or down-regulated by an HNF or that contains an HNF binding site in its promoter region. For example, to ameliorate disease symptoms involving insufficient expression of a gene and/or an inadequate amount of a functional protein in a subject, a gene therapeutic or a protein therapeutic can be administered to the subject. Alternatively, an agent (e.g. strong promoter) that upregulates the expression of a subject's endogenous, functional gene can be a useful therapeutic.

In another preferred embodiment, the pharmaceutical composition is comprised of an antagonist of a disease causing (e.g. mutant) HNF bioactivity or of a disease causing bioactivity encoded by a gene that is up-or down-regulated by an HNF or that contains an HNF binding site in its promoter region. For example, to ameliorate disease symptoms involving expression of a mutant gene or over-expression of a normal gene in a subject, a therapeutically effective amount of an antisense, ribozyme or triple helix molecule to reduce or prevent gene expression, as described herein, may be administered to the subject. Alternatively, to ameliorate disease symptoms involving regulation via a protein of an upstream or downstream element in a biochemical pathway (e.g. initiation or regulation of gene transcription), a therapeutically effective amount of an antagonist compound (e.g. small molecule, peptide, or peptidomimetic) that can prevent binding of the wildtype protein to the nucleic acid, can induce a therapeutic effect. Further, to ameliorate disease symptoms involving a mutant (nonfunctional) protein, a therapeutically effective amount of an antibody, as described herein, may be administered to the subject. Preferably the antibody is administered in a delivery complex or in conjunction with an agent that allows entry of the antibody into cell nuclei.

In yet another aspect, the invention provides assays, for screening test compounds to identify compounds that modulate the expression of a gene or the activity of a gene product involved in diabetes.

A further aspect of the present invention provides methods and kits for determining (e.g. prenatally or postnatally) whether a subject has or is at risk for developing type II diabetes. The method can include detecting, in a biological sample obtained from the subject, the presence or absence of a genetic lesion characterized by at least one of: (i) a mutation of a gene involved in diabetes; (ii) the misexpression of a gene involved in diabetes; or (iii) an error or mutation in the promoter regulating a a gene involved in diabetes that may lead to aberrant expression. In preferred embodiments, detecting the genetic lesion includes ascertaining the existence of at least one of: (a) a deletion of one or more nucleotides from a wildtype gene; (b) an addition of one or more nucleotides to a wildtype gene; (c) a substitution of one or more nucleotides of a wildtype gene; (d) a gross chromosomal rearrangement of a wildtype gene; (e) an alteration in the level of a messenger RNA transcript of a gene; (f) the presence of a non-wild type splicing pattern of a messenger RNA transcript of a gene; (h) a non-wild type level of a protein; and/or (i) an aberrant level of a protein.

For example, detecting the genetic lesion can include: (i) providing probes or primers comprised of an oligonucleotide which hybridizes to a sense or antisense sequence of an HNF gene or gene fragment (wildtype or mutant); or a gene that is up- or down-regulated by an HNF gene; or a gene that contains an HNF binding site in its promoter region or a 5' or 3' flanking sequence of such a gene; (ii) contacting the probes or primers to an appropriate nucleic acid containing biological sample obtained from the subject; and (iii) detecting, by hybridization of the probes or primers to the nucleic acid, the presence or absence of the genetic lesion.

In a preferred embodiment, the diagnostic methods and/or kits utilize a set of primers for amplifying (e.g. via PCR or LCR) at least one region of an HNF gene or a gene that is up-or down-regulated by an HNF gene or a gene that contains an HNF binding site in its promoter region that may contain a mutation, and means for analyzing the amplification product for differences (e.g. mutations) from the normal, wildtype coding sequence.

In another preferred embodiment, the diagnostic methods and/or kits utilize a probe to determine its ability to hybridize under appropriately stringent conditions to a complementary nucleic acid sequence in the biological sample, wherein an inability of a probe, which is comprised of a wildtype HNF sequence or a wildtype sequence of a gene that is up- or down-regulated by an HNF gene or a gene that contains an HNF binding site in its promoter region to hybridize to the sample nucleic acid is indicative of the presence of a mutation in the sample nucleic acid; or the ability of a probe, which is comprised of a mutant HNF sequence or a wildtype sequence of a gene that is up- or down-regulated by an HNF gene or a gene that contains an HNF binding site in its promoter region to hybridize to the sample nucleic acid is indicative of the presence of a mutation in the sample nucleic acid.

In yet a further preferred embodiment, the diagnostic methods and kits employ at least one antibody to at least one epitope, which is characteristic of a wildtype or mutant HNF protein or a wildtype or mutant gene product of a gene that is up- or down-regulated by an HNF gene or a gene that contains an HNF binding site in its promoter region, in an immunoassay procedure to detect the presence of a type II diabetes causing mutation in a biological sample obtained from a subject.

Other features and advantages of the invention will be apparent from the following detailed description and claims.

3. BRIEF DESCRIPTION OF THE FIGURES

Figure 1:
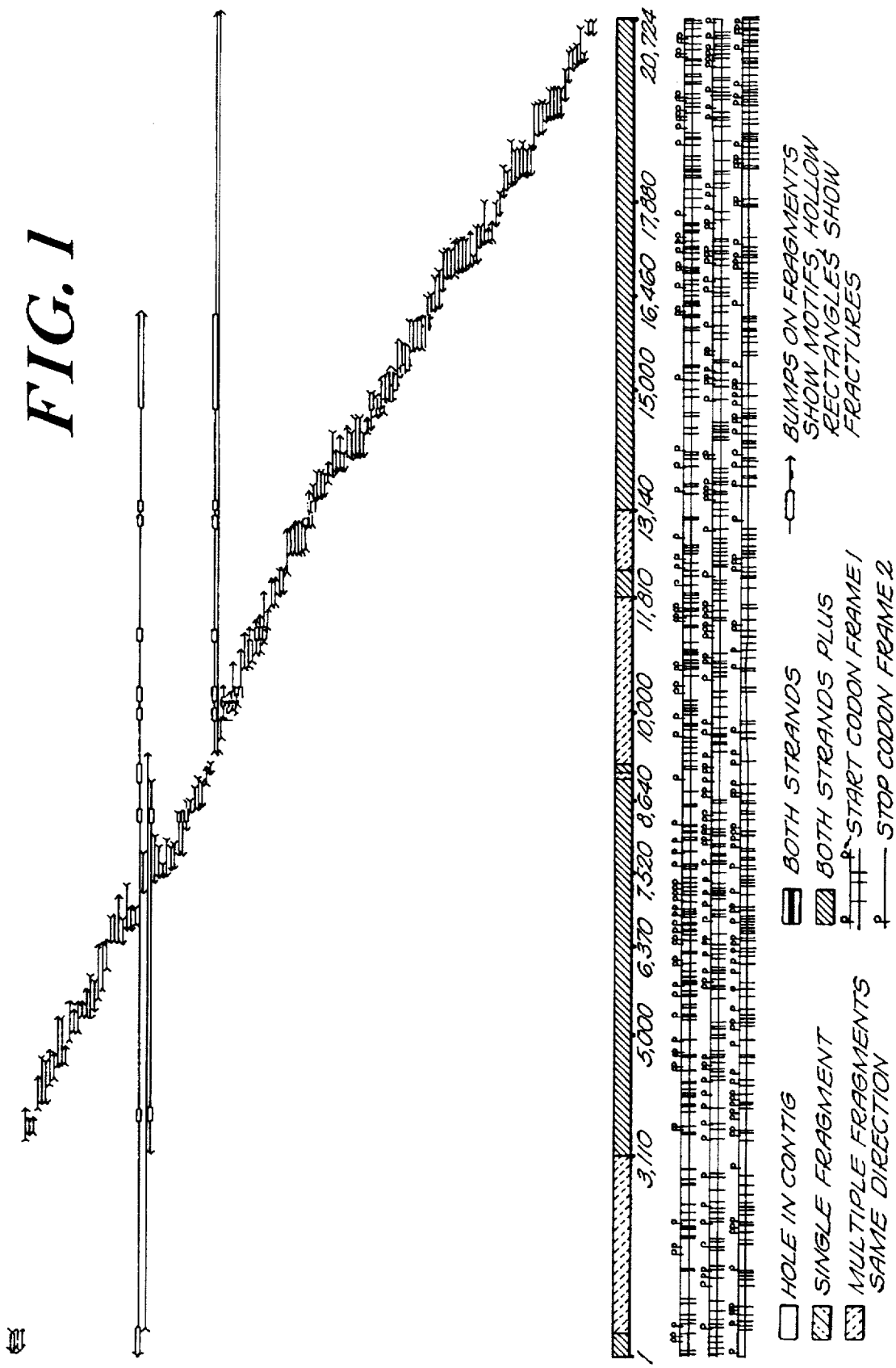
FIG. 1 is a positional map of the cosmid contigs comprising the HNF1 genomic DNA isolated from a subject affected with type II diabetes. The contigs are contained in a BAC clone, that was deposited with the American Type Culture Collection (ATCC) on Nov. 12, 1996 and has been assigned ATCC designation number 97787.
Figure 2:
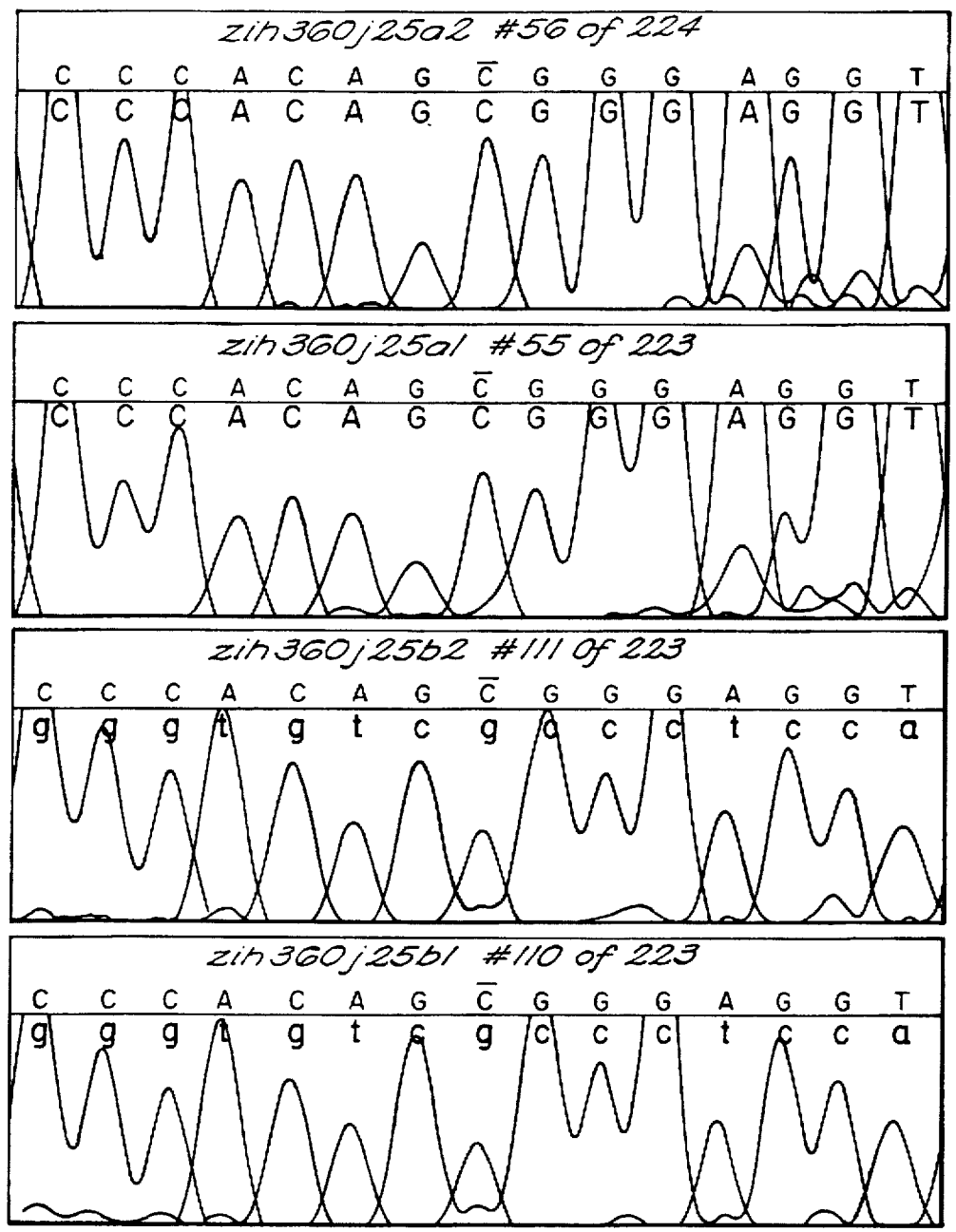
FIG. 2 is an interpreted tracing of a chromatogram of a region of DNA within a portion of exon 2 of the hHNF1 gene (nucleotides 407–421) obtained from a normal individual (i.e. not affected with type II diabetes) from a type II diabetes family. The peptide and corresponding nucleic acid show identity with the wildtype HNF1 sequence.
Figure 3:
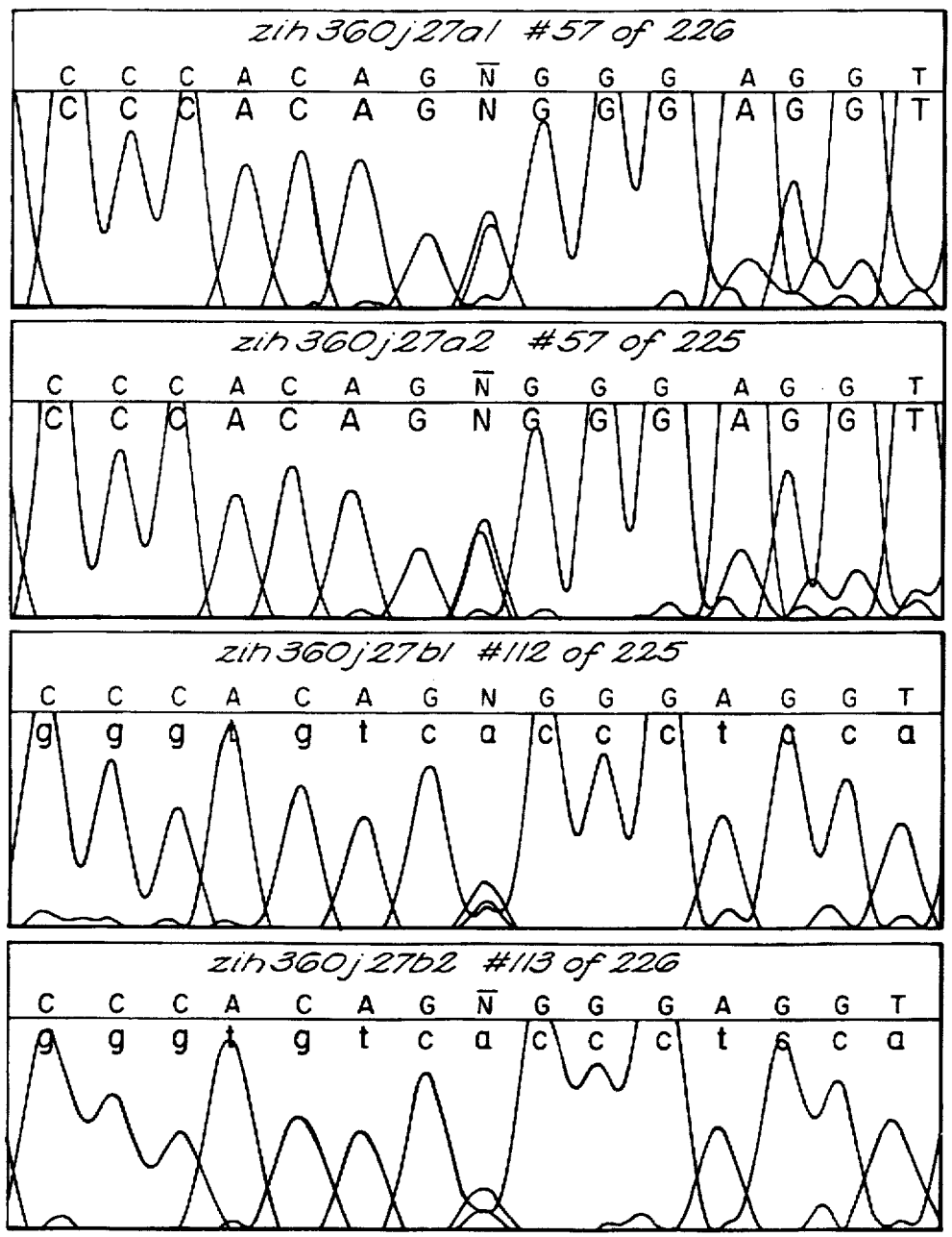

FIG. 3 is an interpreted tracing of a chromatogram of the same region of the hHNF1 gene as described in FIG. 2, but this time the DNA was obtained from an individual affected with type II diabetes. The peptide and corresponding nucleic acid show the heterozygous point mutation, cytosine/thymine (C/T), which results in an amino acid replacement from arginine to tryptophan at position 131 of the hHNF1 protein.

Figure 4:
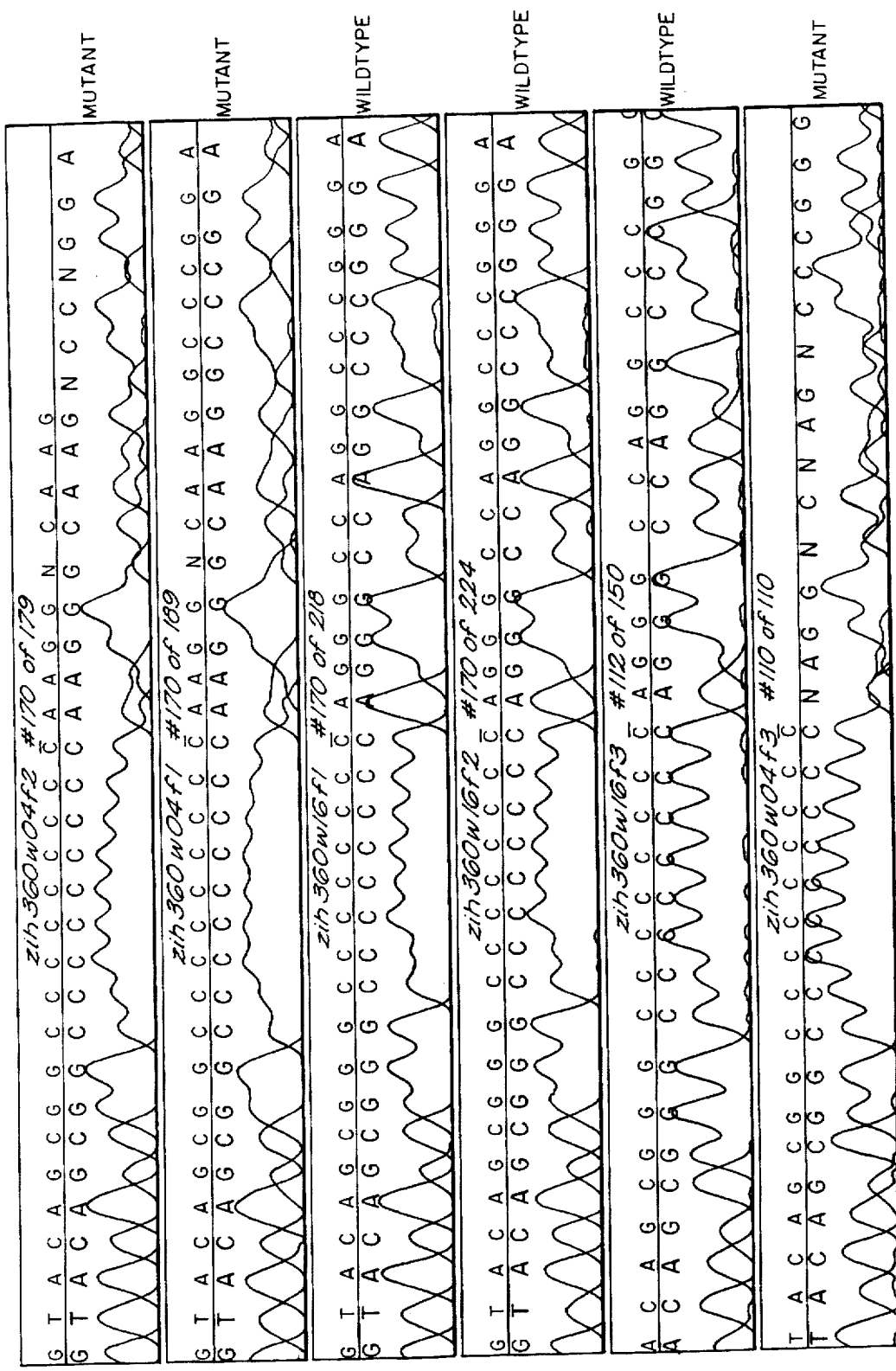

FIG. 4 is an interpreted tracing of a chromatogram of a region of DNA within a portion of exon 4 of the hHNF1 gene obtained from an individual affected with type II diabetes. The peptide and corresponding nucleic acid show the insertion of a cytosine (C) at position 895 as compared to the wildtype HNF1 DNA sequence.

Figure 5:
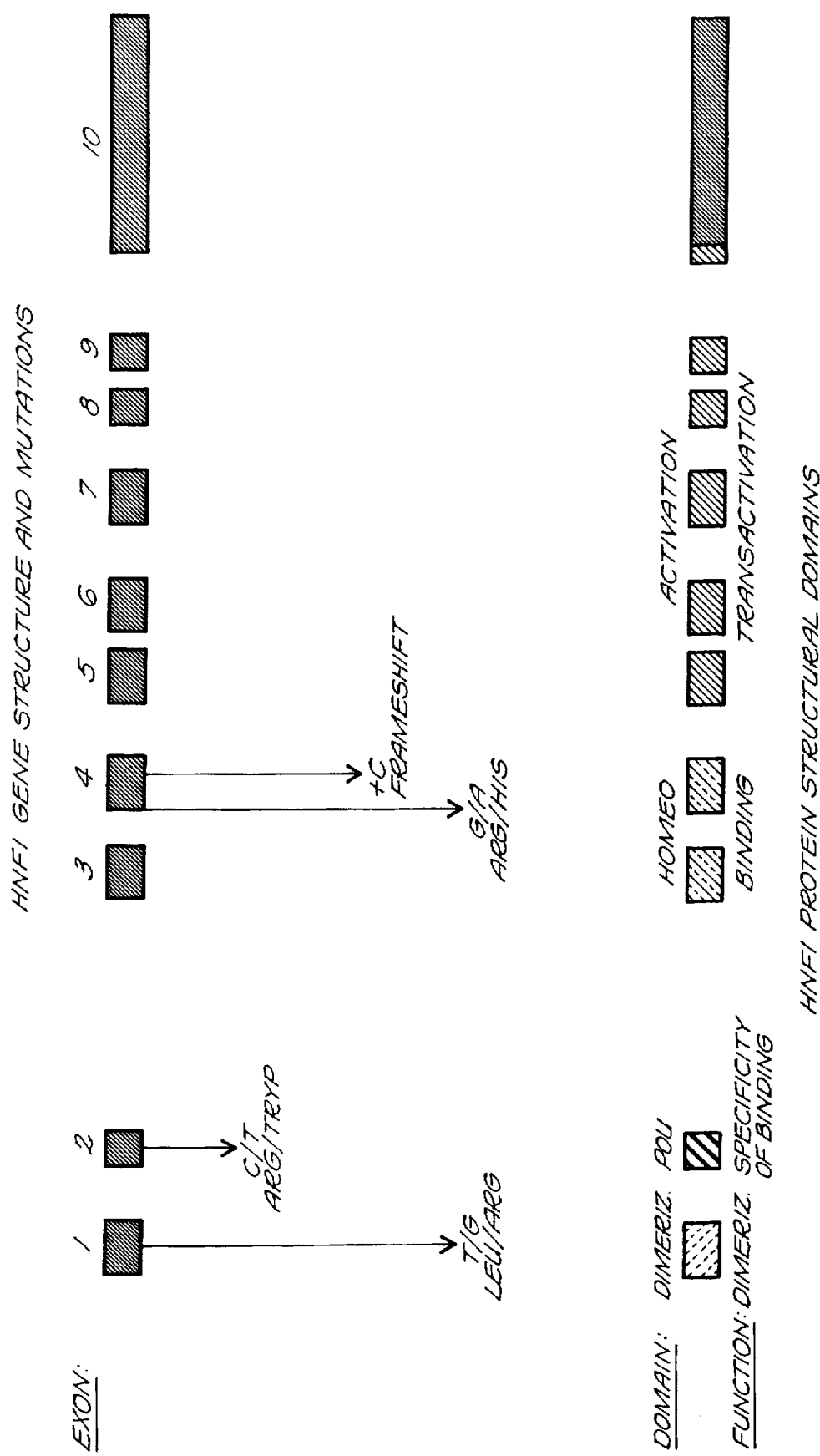

FIG. 5 is a schematic representation of the human HNF1 gene structure and mutations. Top: Representation of the genomic structure of the HNF1 gene. The dark boxes represent the exons and the horizontal lines represent the introns. The arrows indicated the mutations found in diabetics that segregate with disease. Exon 1 contains a mutation from T to G in position 343 of the cDNA which changes the amino acid from leucine to arginine. Exon 2 contains a mutation at position 414 from C to T which converts the arginine to tryptophan. Exon 4 contains two different mutations one at position 838 of the cDNA from a G to an A which changes the amino acid from arginine to histidine. The other mutation in exon 4 is an insertion of a C at position 895 of the cDNA which not only changes the open reading frame of the cDNA, but also introduces a stop codon (at position 968) which produces a truncated protein. Bottom: Representation of the functional domains of the exons of the HNF1 gene.

4. DETAILED DESCRIPTION OF THE INVENTION

4.1. General

As further shown in the following Examples, it has been found that certain mutations in the human HNF1 gene can cause diabetes. The diabetic families that contain these mutations are characterized by both early onset of diabetes and a defect in insulin secretion.

Hepatic Nuclear Factor (HNF) cDNAs are coded and represent different genes. HNF1 maps to chromosome 12, vHNF1 maps to chromosome 17, HNF4 alpha maps to chromosome 20 and finally HNF4 gamma maps to chromosome 8. HNF1 and vHNF1 are homologous to each other, regulate some of the same genes and have similar tissues expression patterns. HNF4 alpha and HNF4 gamma are homologous to each other. HNF4 alpha and HNF4 gamma have an overlapping, but not identical expression pattern. The multiple isoforms might explain very complex forms of regulations by these transcription factors in different tissues. The redundancy of these transcription factors would appear to allow for complementation of these genes with respect to each other when one of them is defective (e.g. in a type II diabetic subject).

HNF 1 is a crucial transcriptional activator of many hepatic genes and is also expressed and activates genes in kidney, stomach and pancreas. HNF1 is comprised of three functional domains. Exon 1 of the HNF1 gene encodes the domain necessary for dimerization. Exons 2, 3 and 4 encode the domain required for binding to DNA. Exon 5–10 encode the domain required for transactivation of transcription (C.R. Acad. Sci. Paris, Life Science (1993) 316:385–94). HNF1 regulates transcription of a particular gene by dimerizing and binding upstream of the gene's promoter. The transcription factor can form homodimers with itself or can heterodimerize with the protein product of a different gene known as vHNF1. Although different, vHNF1 is very homologous to HNF1, especially at the binding domain which is 93% homologous. HNF1 and vHNF1 recognize the same binding site. In addition, both HNF1 and vHNF1 have various isoforms generated by alternative splicing and use of different polyadenylation sites. These isoforms can form homodimers or various combinations of heterodimers. Different isoforms can regulate different subsets of genes in different tissues. Defects in the regulation of certain genes in pancreatic islets and/or liver can cause or contribute to the defects in insulin secretion characteristic of type II diabetes.

HNF1 is one of a series of transcription factors that function in a cascade form to regulate gene expression in cells. A hierarchy of liver-enriched transcription factors in this cascade plays an important role in activating expression of many hepatic genes. In particular hepatocyte nuclear factor 4 (HNF4) is a major activator of the gene encoding HNF1. HNF1 itself is known to activate expression of more than 20 liver genes and also negatively regulates its own expression and that of HNF4. There are binding sites for HNF1 upstream of both the HNF1 and HF4 gene (W. Zhong et al. Mol Cell Biol. 14: 7276 (1994)). It is possible that some of the genes regulated by either or both of these transcription factors is also involved in diabetes.

HNF4 belongs to the family of nuclear hormone receptors whose activation capabilities are induced by the binding of a ligand. This family of regulatory proteins share common mechanistic features in that they are transcriptionally inactive within the cell until exposed to a ligand. Occupancy by hormone results in transformation of the receptor to an activated state, thus allowing it to productively interact with specific DNA sequences in the regulatory regions of target genes. The nuclear receptors are characterized by a central DNA binding domain which targets the receptor to specific DNA sequences known as hormone response elements (HREs). The DNA binding domains of these receptors are related. The C-terminal half of the receptor encompasses the ligand-binding domain (LBD). Upon ligands binding, the receptor shifts to a transcriptionally active state.

The ligand for HNF4 has yet to be identified. Therefore HNF4 is considered an "orphan receptor". Orphan receptors are found in every metazoan species. It is expected that some may interact with novel ligands, while others may represent constitutive activators/repressors or factors whose activity is modulated by postranslational modification.

Nuclear hormone receptors bind as dimers and can heterodimerize with other members of the same family. HNF4 is unusual in that it cannot dimerize with other members of the family. The nuclear hormone receptors superfamily can also be divided into two broad families; the steroid receptor family and the nonsteroid receptor family. The ligands for this last family are chemically diverse and may be activated by metabolic pathways within the target cells.

Type II diabetes is characterized by a patient's inability to respond to insulin and/or insufficient insulin secretion. Insulin exerts a dominant effect on the regulation of glucose homeostasis. In the liver, insulin inhibits the production of glucose by inhibiting gluconeogenesis and glycogenolysis. Insulin is thought to act by causing cells to absorb glucose from the blood stream. Once absorbed, the liver converts glucose to glycogen. The liver supplies glucose by converting glycogen stores to glucose. Insulin also has a major role in the regulation of protein and lipid metabolism through a variety of actions that affect the flux of protein and lipid substrates.

The glycolytic pathway is central in the understanding of the lack of glucose homeostasis in diabetes. There is very tight cellular control of glycolysis. This control is carried by the regulatory inhibition by certain glycolytic enzymes depending on the level of various glucose degradation products. Since the degradation products of glucose are also important precursors or intermediates in other aspects of metabolism, the regulatory enzymes in carbohydrate catabolism also recognize and respond to appropriate signals from other metabolic pathways.

Some of the enzymes involved in the degradation of glucose are known to be regulated and/or contain binding sites for HNF1 and/or HNF4. The first step in the degradation of glucose is the phosphorylation of glucose to glucose-6-phosphate and is carried out by an enzyme called glucokinase. The hormone insulin, secreted by the pancreas into the blood whenever the blood glucose concentration is high, stimulates the synthesis of glucokinase. In the diabetic condition, which is characterized by a defect in insulin secretion and/or amount of insulin, glucokinase is typically also deficient.

In addition to regulation of the rate of glycolysis through control of the entry of free glucose, the sequence of reactions from glucose to pyruvate is also under biological control. The enzyme that converts phosphoenol pyruvate to pyruvate and ATP is called pyruvate kinase. At high ATP concentrations the affinity of pyruvate kinase for phosphoenol pyruvate is relatively low. Pyruvate kinase is also inhibited by acetyl-CoA and by long chain fatty acids. Therefore, whenever ample fuels are available for respiration, glycolysis is inhibited by the action of pyruvate kinase. Since glucokinase contains HNF1 binding sites at its promoter region and pyruvate kinase contains HNF4 binding sites, modulation of the bioactivity of glucokinase and/or pyruvate kinase can be an effective therapy for type II diabetes.

Additionally, the anabolic enzyme phosphoenolpyruvate carboxykinase which converts phosphoenolpyruvate and carbon dioxide to oxalacetate and GTP is also regulated by HNF1. The pyruvate carboxylase reaction is the most important anaplerotic (filling up) reaction in the liver. Pyruvate carboxylase is also a regulatory enzyme and is stimulated when acetyl-CoA is present.

As mentioned above, insulin has a role in lipid metabolism. Diabetes is associated with lipid related disorders such as obesity, elevated cholesterol and triglycerides. Both HNF1 and HNF4 regulate the expression of apolipoproteins. HNF1 is known to regulate apolipoproteins B and HNF4 is known to regulate the expression of apolipoprotein A and C. Apolipoproteins are blood plasma proteins which carry lipids from the liver to other organs. As mentioned above, when there is an excess of glucose in the blood, the liver produces lipids instead of glucose. High levels of circulating insulin causes the liver to increase the production of lipids. Therefore, metabolism of lipids and carbohydrates is intimately related.

The regulation of the above-mentioned proteins by both HNF1 and HNF4 suggests a major involvement of these transcription factors in the regulation of both the catabolic and anabolic pathways that lead to and from glucose as well as lipid metabolism. As mentioned above, the ligands for nuclear hormone receptors may be activated by metabolic pathways within the target cells. One such pathway could be the one involved in glucose metabolism. Therefore, identifying the ligand for HNF4 could lead to a therapeutic target for diabetes.

Assays for identifying genes which are up-or down-regulated by HNF1 and/or that contain an HNF1 binding site in its promoter region can be identified as described further in the following Examples. In addition, the following Table 1 provides a list of genes that are known to be either up- or down-regulated by HNF1 and/or that contain HNF1 binding sites in their promoter region. These genes and encoded proteins and/or molecules that can interact with these genes and/or proteins each alone or in any combination can modulate the expression of a gene or genes or the activity of a gene product or gene products involved in diabetes and therefore can provide useful therapeutics for Type II diabetes.

TABLE 1

| PROTEINS INVOLVED IN CARBOHYDRATE METABOLISM | CITATION |
|---|---|
| Liver specific glucokinase | J. Biol. Chem. 264:15936–1592 (1989) M. A. Magnuson et al. |
| Glucose transporter (GLUT2) | Cell 55:282–290 (1988) B. Thorens et al. |
| Insulin | PNAS 89:7300–7304 (1992) L. Emens et al. |
| Phosphoenolpyruvate carboxykinase | Mol. Cell Biol. 14:7124–7133 (1994) O. Yanuka-kashles et al. |
| Pyruvate kinase | J. Biol. Chem. 268:13769–13772 (1993) M. H. Ciuf |
| Albumin | Diabetes 45:1217–1222 (1996) G. Barrera-Hernandez |
| Aldolase B | Mol. Cell Biol. 16:76–85 (1996) M. Salminen et al. |
| UDP-N-acetylglucosamine | Eur. J. Biochem. 233:18–26 (1995) H. Saito et al. |
| Alcohol dehydrogenase genes (ADH1, 2 and 3) | Pharmacogenetics 2:185–196 (1992) H. J. Edenberg et al. |
| Cytochrome P-450 | FASEB J. 10:1112–1117 (1996) F. J. Gonzales et al. |
| Proteins involved in amino acid metabolism | |
| Aminopeptidase N (APN) | J. Biochem. 312:31–37 (1995) J. Olsen et al. |
| Phenylalanine hydroxylase | Mol. Cell Biol. 16:3125–3137 D. M. Faust et al. |
| Tyrosine aminotransferase | Scheweizer-Goyer et al. |
| Proteins involved in lipid metabolism | |
| hepatic triglyceride lipase (HTGL) | Biochemistry 32:9657–9667 (1993) P. Cardot et al. |
| Apolipoprotein B | Biochemistry 32:9080–9093 (1993) P. Cardot et al. |
| Apolipoprotein A-II | J. Biol. Chem 266:11676–11685 (1991) J. Chambaz et al. |
| Cholesterol 7 alpha-hydrolase | Arch. Biochem. Biophys. 306:451–460 (1993) M. Crestani et al. |
| Plasma proteins | |
| Fibrinogen | J. Biol. Chem. 270:28342–28349 (1995) C. H. Hu et al. |
| alpha-1-microglobulin/bikunin precursor | Nucleic Acids. Res. 23:395–404 (1995) P. Rouet et al. |
| C4b-binding protein | J. Biochem. 308:613–621 (1995) N. Arenzana et al. |
| insulin-like growth factor (IGF-I) | DNA Cell. Biol. 12:283–289 (1993) D. R. Powell et al. |
| Alpha-fetoprotein | Mol. Cell Biol. 13:1619–1633 (1993) D. Bernier et al. |
| Adhesion Molecule | |
| Neural cell adhesion molecule (N-CAM) | Mol. Carcinog. 6:245–254 (1993) R. R. Hoyt |

4.2 Definitions

For convenience, the meaning of certain terms and phrases employed in the specification, examples, and appended claims are provided below.

The term "agonist", as used herein, is meant to refer to an agent that supplements or potentiates the bioactivity of a functional HNF gene or protein or of a polypeptide encoded by a gene that is up- or down-regulated by an HNF polypeptide and/or a polypeptide encoded by a gene that contains an HNF binding site in its promoter region.

The term "antagonist", as used herein, is meant to refer to an agent that decreases or inhibits the bioactivity of a functional HNF gene or protein or that supplements or potentiates the bioactivity of a non-functional (mutant) HNF gene or protein. Alternatively, an antagonist can decrease or inhibit the bioactivity of a functional gene or polypeptide encoded by a gene that: i) is up- or down-regulated by an HNF polypeptide and/or ii) contains an HNF binding site in its promoter region. An antagonist may also supplement or potentiate the bioactivity of a non-functional (mutant) gene or polypeptide encoded by a gene that: i) is up- or down-regulated by an HNF polypeptide and/or ii) contains an HNF binding site in its promoter region. "Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject HNF polypeptides with a second amino acid sequence defining a domain (e.g. polypeptide portion) foreign to and not substantially homologous with any domain of one of the HNF proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X—HNF—Y, wherein HNF represents a portion of the protein which is derived from one of the HNF proteins, and X and Y are independently absent or represent amino acid sequences which are not related to one of the HNF sequences in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an HNF polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Diabetes" is a term used to refer to disorders, which relate to alterations in glucose homeostasis. In the mildest forms of diabetes, this alteration is detected only after challenge with a carbohydrate load, while in moderate to severe forms of disease, hyperglycemia is always present. Type I diabetes, insulin dependent diabetes mellitus or IDDM, is the result of a progressive autoimmune destruction of the pancreatic β-cells with subsequent insulin deficiency. The more prevalent Type II, non-insulin dependent diabetes mellitus or NIDDM, is associated with peripheral insulin resistance, elevated hepatic glucose production, and inappropriate insulin secretion. Type II diabetes that develops during the age of 20—30 years old and is associated with chronic hyperglycemia and monogenic inheritance is referred to as maturity onset diabetes of the young (MODY). Other forms of Type II diabetes develop in an individual sometime after 20–30 years of age (e.g. late-onset NIDDM).

"Differential expression", as used herein, refers to both quantitative as well as qualitative differences in a genes' temporal and/or tissue expression patterns. Differentially expressed genes may represent "fingerprint genes," and/or "target genes."

"Fingerprint gene," as used herein, refers to a gene whose expression pattern may be utilized as part of a prognostic or diagnostic diabetes evaluation, or which, alternatively, may be used in methods for identifying compounds useful for the treatment of diabetes.

As used herein, the term "hepatic nuclear factor (HNF) gene" or "recombinant HNF gene" refers to a nucleic acid molecule (e.g. genomic DNA, cDNA or mRNA) encoding one of the HNF polypeptides of the present invention, including both exon and (optionally) intron sequences. A "recombinant gene" refers to nucleic acid encoding an HNF polypeptide and comprising an HNF-encoding exon sequence, though it may optionally include intron sequences which are either derived from a chromosomal HNF gene or from an unrelated chromosomal gene. The term "intron" refers to a DNA sequence present in a given HNF gene which is not translated into protein and is generally found between exons.

An "HNF polypeptide" refers to a hepatic nuclear factor and functional fragments thereof. Hepatic Nuclear Factor 1 (HNF1 or HNF1α also named HP-1, LFB1 or APF) is a transcription factor that binds to the promoters or enhancers of a variety of genes, particularly genes expressed exclusively in the liver, although HNF-1 has also been found to be expressed in kidney, intestine, stomach, pancreas, spleen and testis. Variant HNF 1 (vHNF1, also known as HNF1β or LFB3) is a nuclear factor that binds the same sequence elements in numerous liver specific genes as is bound by HNF-1 (Ringeisen, F. et al., (1993) *J. Bio. Chem.* 268.25706–25711). Two forms of vHNF1 have been described and are derived from alternative splicing from a common premessenger RNA, and have been called vHNF1-A (GenBank Accession No. S15342) and vHNF1-B. vHNF1-A has been reported to be a stronger transactivator than vHNF1-B. cDNAs from human liver encoding several isoforms of HNF1 (i.e. HNF1-B and -C) and vHNF1 (vHNF1-C) generated by the differential use of polyadenylation sites and by alternative splicing have been reported (Bach. I. and M. Yaniv (1993) *The Embo Journal* 12. 4229–4242). The isoforms all contain different C-terminal domains. As used herein. the term HNF-1 is intended to encompass HNF-1-A. -B. and -C. as well as vHNF1-A. -B. and -C. HNF3 is another liver enriched transcription factor that is also important in liver -specific gene expression. HNF4 is yet another liver enriched transcription factor. cDNA encoding rat HNF4 is described in International Patent Application WO 92/11365. Human hepatocyte nuclear factor 4 isoforms (e.g. HNF4α-2, a splice variant of HNF4α-4; and HNF4γ) are reported in Drewes. T. et al.. (1 996) *Mol. and Cell. Biol.* 16:925–931.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid. then the molecules are homologous at that position. A degree of homology between sequences is a function of the number of matching or homologous positions shared by the sequences. An "unrelated" or "non-homologous" sequence shares less than 40% identity. though preferably less than 25% identity. with one of the HNF sequences of the present invention.

The term "interact" as used herein is meant to include detectable interactions (e.g. biochemical interactions) between molecules. such as can be detected using. for example. a yeast two hybrid assay. The term interact is also meant to include "binding" interactions between molecules. Interactions may. for example. be protein-protein or protein-nucleic acid in nature.

The term "isolated" as used herein with respect to nucleic acids. such as DNA or RNA. refers to molecules separated from other DNAs. or RNAs. respectively. that are present in the natural source of the macromolecule. For example. an isolated nucleic acid encoding one of the subject HNF polypeptides preferably includes no more than 10 kilobases (kb) of nucleic acid sequence which naturally immediately flanks the HNF gene in genomic DNA. more preferably no more than 5 kb of such naturally occurring flanking sequences. and most preferably less than 1.5 kb of such naturally occurring flanking sequence. The term isolated as used herein also refers to a nucleic acid or peptide that is substantially free of cellular material. viral material. or culture medium when produced by recombinant DNA techniques. or chemical precursors or other chemicals when chemically synthesized. Moreover. an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation (i.e.. activation or stimulation (e.g.. by agonizing or potentiating)) and downregulation (i.e. inhibition or suppression (e.g. by antagonizing. decreasing or inhibiting) the expression of a gene or genes or the activity of a gene product or gene products involved in diabetes.

The "non-human animals" of the invention include mammalians such as rodents. non-human primates. sheep. dog. cow. chickens. amphibians. reptiles. etc. Preferred non-human animals are selected from the rodent family including rat and mouse. most preferably mouse. though transgenic amphibians. such as members of the Xenopus genus. and transgenic chickens can also provide important tools for understanding and identifying agents which can affect. for example. embryogenesis and tissue formation. The term "chimeric animal" is used herein to refer to animals in which the recombinant gene is found. or in which the recombinant is expressed in some but not all cells of the animal. The term "tissue-specific chimeric animal" indicates that one of the recombinant HNF gene is present and/or expressed or disrupted in some tissues but not others.

As used herein. the term "nucleic acid" refers to polynucleotides such as deoxyribonucleic acid (DNA). and. where appropriate. ribonucleic acid (RNA). The term should also be understood to include. as equivalents. analogs of either RNA or DNA made from nucleotide analogs. and. as applicable to the embodiment being described. single (sense or antisense) and double-stranded polynucleotides.

A "pathway gene" as used herein is defined via the ability of its product to interact with another gene product (e.g. HNF1) involved in diabetes. Pathway genes may also exhibit target gene and/or fingerprint gene characteristics.

As used herein. the term "promoter" means a DNA sequence that regulates expression of a selected DNA sequence operably linked to the promoter. and which effects expression of the selected DNA sequence in cells. The term encompasses "tissue specific" promoters. i.e. promoters. which effect expression of the selected DNA sequence only in specific cells (e.g. cells of a specific tissue). The term also covers so-called "leaky" promoters. which regulate expression of a selected DNA primarily in one tissue. but cause expression in other tissues as well. The term also encompasses non-tissue specific promoters and promoters that constitutively express or that are inducible (i.e. expression levels can be controlled).

The terms "protein". "polypeptide" and "peptide" are used interchangeably herein when referring to a gene product.

The term "recombinant protein" refers to a polypeptide of the present invention which is produced by recombinant DNA techniques. wherein generally. DNA encoding an HNFpolypeptide is inserted into a suitable expression vector which is in turn used to transform a host cell to produce the heterologous protein. Moreover. the phrase "derived from". with respect to a recombinant HNF gene. is meant to include within the meaning of "recombinant protein" those proteins having an amino acid sequence of a native HNF protein. or an amino acid sequence similar thereto which is generated by mutations including substitutions and deletions (including truncation) of a naturally occurring form of the protein.

"Small molecule" as used herein. is meant to refer to a composition. which has a molecular weight of less than about 5 kD and most preferably less than about 4 kD. Small molecules can be nucleic acids. peptides. polypeptides. peptidomimetics. carbohydrates. lipids or other organic or inorganic molecules.

As used herein. the term "specifically hybridizes" or "specifically detects" refers to the ability of a nucleic acid molecule of the invention to hybridize to at least approximately 6. 12. 20. 30. 50. 100. 150. 200. 300. 350. 400 or 425 consecutive nucleotides of a vertebrate. preferably an HNF gene.

"Target gene". as used herein. refers to a gene involved in diabetes such that modulation of the level of target gene expression or of target gene product activity may act to ameliorate a diabetic condition. Compounds that modulate target gene expression or activity of the target gene product can be used in the treatment of diabetes.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the HNF genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of HNF protein.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an HNF polypeptide or, in the case of anti-sense expression from the transferred gene, the expression of a naturally-occurring form of the HNF protein is disrupted.

As used herein, the term "transgene" means a nucleic acid sequence (encoding, e.g., one of the HNF polypeptides, or an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the HNF protein, e.g. either agonistic or antagonistic forms. However, transgenic animals in which the recombinant HNF gene is silent are also contemplated, as for example, the FLP or CRE recombinase dependent constructs described below. Moreover, "transgenic animal" also includes those recombinant animals in which gene disruption of one or more HNF gene is caused by human intervention, including both recombination and antisense techniques.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Therapeutics that modulate the expression of a gene or the activity of a gene product involved in diabetes will now be described in further detail.

4.3 Gene Therapeutics

One aspect of the invention pertains to the administration of isolated nucleic acids e.g. encoding an HNF polypeptide or a gene that is up- or down-regulated by an HNF polypeptide and or that contains an HNF binding site in its promoter region and/or equivalents of such nucleic acids to treat a diabetic subject. The term equivalent is understood to include nucleotide sequences that are not identical to the reported hHNF nucleic acid sequences or a known gene that is up- or down-regulated by an HNF polypeptide and or that contains an HNF binding site in its promoter region, but that encodes a polypeptide having the same or similar activity as the known protein. Equivalent nucleotide sequences will include sequences that differ by one or more nucleotide substitution, addition or deletion, such as allelic variants of the reported sequence.

Preferred nucleic acids are obtained from vertebrates. Particularly preferred vertebrate nucleic acids are mammalian. Preferred nucleic acids encode an HNF1 or HNF4 polypeptide comprising an amino acid sequence, which is at least 90% homologous and more preferably 94% homologous with the reported amino acid sequences of hHNF1 or hHNF4.

Appropriate stringency conditions for identifying homologs of known genes, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Nucleic acids having a sequence that differs from the reported sequences due to degeneracy in the genetic code are also within the scope of the invention. Such nucleic acids encode functionally equivalent peptides (i.e., peptides having the same biological activity) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an polypeptide. However, it is expected that DNA sequence polymorphisms that do lead to changes in the amino acid sequences of the subject polypeptides will exist among mammalians. One skilled in the art will appreciate that these variations in one or more nucleotides (e.g., up to about 3–5% of the nucleotides) of the nucleic acids encoding polypeptides may exist among individuals of a given species due to natural allelic variation.

Nucleic acids can be obtained from mRNA present in any of a number of eukaryotic cells. It should also be possible to obtain nucleic acids of the present invention from genomic DNA from both adults and embryos. For example, a gene can be cloned from either a cDNA or a genomic library in accordance with protocols described herein, as well as those generally known to persons skilled in the art. Examples of tissues and/or libraries suitable for isolation of the subject nucleic acids include liver, pancreatic islet cells and lymphoblasts, among others. A cDNA can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a protein can also be cloned using established polymerase chain reaction techniques in accordance with the nucleotide sequence information provided by the invention. The nucleic acid of the invention can be DNA or RNA.

For gene therapy, preferably the gene is administered to a subject in an expression vector, i.e. a nucleic acid encoding a polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of an HNF polypeptide or a polypeptide encoded by a gene that is up- or down-regulated by an HNF polypeptide and or that contains an HNF binding site in its promoter region, or alternatively, encoding a peptide which is an antagonistic form of the HNF protein or a polypeptide encoded by a gene that is up- or down-regulated by an HNF polypeptide and or that contains an HNF binding site in its promoter region. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject HNF proteins or a polypeptide encoded by a gene that is up- or down-regulated by an HNF polypeptide and or that contains an HNF binding site in its promoter region. Thus, another aspect of the invention features expression vectors for in vivo or in vitro transfection and expression of an HNF polypeptide or a polypeptide encoded by a gene that is up- or down-regulated by an HNF polypeptide and or that contains an HNF binding site in its promoter region, in particular cell types so as to reconstitute the function of, or alternatively, abrogate the function of an HNF bioactivity or the bioactivity of a polypeptide encoded by a gene that is up- or down-regulated by an HNF polypeptide and or that contains an HNF binding site in its promoter region. This could be desirable, for example, when the naturally-occurring form of the protein is misexpressed; or to deliver a form of the protein which alters gene transcription in a tissue.

In addition to viral transfer methods, such as those illustrated above, non-viral methods can also be employed to cause expression of a subject polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject gene by the targeted cell. Exemplary targeting means of this type include liposomal derived systems, poly-lysine conjugates, and artificial viral envelopes.

4.4. Peptide and Small Molecule Therapeutics

The present invention also makes available isolated HNF polypeptides or polypeptides encoded by genes that are up- or down-regulated by an HNF polypeptide and or that contain an HNF binding site in their promoter region, which are isolated from, or otherwise substantially free of other cellular proteins, especially other signal transduction factors and/or transcription factors which may normally be associated with the subject polypeptide. The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified preparations will lack any contaminating proteins from the same animal from which the subject polypeptide is normally produced, as can be accomplished by recombinant expression of, for example, a human protein in a non-human cell.

Full length proteins or fragments corresponding to one or more particular motifs and/or domains or to arbitrary sizes, for example, at least 5, 10, 25, 50, 75, 100, 125, 150 amino acids in length are within the scope of the present invention.

For example, isolated HNF1 polypeptides can include all or a portion of an amino acid sequences corresponding to an HNF1 polypeptide described in Bach, I. et al., (1990) *Genomics* 8:155–164. Isolated peptidyl portions of HNF proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "functional") or mutant HNF protein or of a polypeptide encoded by a gene that is up- or down-regulated by an HNF polypeptide and or that contains an HNF binding site in its promoter region.

According to the present invention, a polypeptide has biological activity if it is a specific agonist or antagonist. For example, a polypeptide agonist can effect increased expression of a functional HNF gene; and/or increased activity of a functional HNF protein. Further, a polypeptide antagonist can effect decreased expression of a functional or mutant HNF gene or decreased activity of a functional or mutant HNF protein.

The present invention further pertains to methods of producing the subject polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject HNF polypeptides or a polypeptide encoded by a gene that is up- or down-regulated by an HNF polypeptide and or that contains an HNF binding site in its promoter region, which function in a limited capacity as one of either an agonist (mimetic) or an antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of HNF proteins.

Homologs of each of the subject proteins can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the protein can be generated which are able to inhibit the function of the naturally occurring form of the protein, such as by competitively binding to a downstream or upstream member of the biochemical pathway, which includes the HNF protein. In addition, agonistic forms of the protein may be generated which are constitutively active. Thus, the HNF protein and homologs thereof or a polypeptide encoded by a gene that is up- or down-regulated by an HNF polypeptide and or that contains an HNF binding site in its promoter region, as provided herein may be either positive or negative regulators of gene expression.

The recombinant polypeptides of the present invention also include homologs of known proteins, such as versions of those protein which are resistant to proteolytic cleavage, as for example, due to mutations which alter ubiquitination or other enzymatic targeting associated with the protein.

Polypeptide agonists or antagonists as discussed herein may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysin, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, WH Freeman and Co.: 1981). Whether a change in the amino acid sequence of a peptide results in a functional homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject agonist or antagonist polypeptides as well as truncation mutants, and is especially useful for identifying potential variant sequences (e.g. homologs) that are functional in modulating gene expression. The purpose of screening such combinatorial libraries is to generate, for example, novel compounds which can act as either agonists or antagonist, or alternatively, possess novel activities all together.

Likewise, HNF homologs or homologs of a polypeptide encoded by a gene that is up- or down-regulated by an HNF polypeptide and or that contains an HNF binding site in its promoter region, can be generated by the present combinatorial approach to selectively inhibit gene expression. For instance, mutagenesis can provide homologs which are able to bind other signal pathway proteins (or DNA) yet prevent propagation of the signal, e.g. the homologs can be dominant negative mutants. Moreover, manipulation of certain domains of an HNF or a polypeptide encoded by a gene that is up- or down-regulated by an HNF polypeptide and/or that contains an HNF binding site in tis promoter region, by the present method can provide domains more suitable for use in fusion proteins.

In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g. for phage display) containing the set of sequences therein.

There are many ways by which such libraries of potential HNF homologs or a polypeptide encoded by a gene that is up- or down-regulated by an HNF polypeptide and or that contains an HNF binding site in its promoter region can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential sequences. The synthesis of degenerate oligonucleotides is well known in the art (see for example, Narang, S. A. (1983) *Tetrahedron* 39:3; Itakura et al. (1981) *Recombinant DNA, Proc 3rd Cleveland Sympos. Macromolecules*, ed. A. G. Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477). Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87:6378–6382; as well as U.S. Pat. Nos. 5,223,409, 5,198, 346, and 5,096,815).

Likewise, a library of coding sequence fragments can be provided for a clone in order to generate a variegated population of fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of HNF homologs or homologs of polypeptides encoded by a gene that is up- or down-regulated by an HNF polypeptide and or that contains an HNF binding site in its promoter region. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–33 1).

The invention also provides for the identification and/or generation of mimetics, e.g. peptide or non-peptide agents, which are able to disrupt binding of an HNF polypeptide or a polypeptide encoded by a gene that is up- or down-regulated by an HNF polypeptide and or that contains an HNF binding site in its promoter region with either upstream or downstream components. Thus, such mutagenic techniques as described above are also useful to map the determinants of the proteins which participate in protein-protein interactions involved in, for example, binding of the subject polypeptides to proteins which may function upstream (including both activators (enhancers) and repressors of its activity) or to proteins and/or nucleic acids which may function downstream of the polypeptides, whether they are positively or negatively regulated by it. To illustrate, the critical residues of a subject polypeptide which are involved in molecular recognition of a component upstream or downstream of an HNF protein or a polypeptide encoded by a gene that is up- or down-regulated by an HNF polypeptide and or that contains an HNF binding site in its promoter region can be determined and used to generate peptidomimetics which competitively inhibit binding of the authentic protein with that moiety. By employing, for example, scanning mutagenesis to map the amino acid residues of each of the subject proteins which are involved in binding other extracellular proteins, peptidomimetic compounds can be generated which mimic those residues of the protein which facilitate the interaction. Such mimetics may then be used to interfere with the normal function of a protein. For instance, non-hydrolyzable peptide analogs of such residues can be generated using benzodiazepine (e.g.. see Freidinger et al. in *Peptides: Chemistry and Biology*, G. R. Marshall ed.. ESCOM Publisher: Leiden. Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), ketomethylene pseudopeptides (Ewenson et al. (1986) *J Med Chem* 29:295: and Ewenson et al. in *Peptides: Structure and Function* (Proceedings of the 9th American Peptide Symposium) Pierce Chemical Co. Rockland. Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun*, 126:419; and Dann et al. (1986) *Biochem Biophys Res Commun* 134:71).

This invention also pertains to a host cell transfected to express a recombinant form of the subject polypeptides. The host cell may be any prokaryotic or eukaryotic cell. Thus, a nucleotide sequence derived from the cloning of vertebrate proteins, encoding all or a selected portion of the full-length protein, can be used to produce a recombinant form of a polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, p53, WT1, PTP phosphotases, SRC, and the like. Similar procedures, or modifications thereof, can be employed to prepare recombinant polypeptides by microbial means or tissue-culture technology in accord with the subject invention.

The recombinant genes can be produced by ligating nucleic acid encoding a protein, or a portion thereof, into a vector suitable for expression in either prokaryotic cells, eukaryotic cells, or both. Expression vectors for production of recombinant forms of the subject polypeptides include plasmids and other vectors. For instance, suitable vectors for the expression of a polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, an HNF polypeptide is produced recombinantly utilizing an expression vector generated by sub-cloning the coding sequence of an HNF gene.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant polypeptides by the use of a baculovirus expression system. Examples of such baculovirus expression systems include pVL-derived vectors (such as pVL 1392, pVL 1393 and pVL941), pAcUW-derived vectors (such as pAcUW1), and pBlueBac-derived vectors (such as the β-gal containing pBlueBac III).

When it is desirable to express only a portion of a protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below, could be used to produce recombinant proteins.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a protein. For example, the VP6 capsid protein of rotavirus can be used as an immunologic carrier protein for portions of the polypeptide, either in the monomeric form or in the form of a viral particle. The nucleic acid sequences corresponding to the portion of a subject protein to which antibodies are to be raised can be incorporated into a fusion gene construct which includes coding sequences for a late vaccinia virus structural protein to produce a set of recombinant viruses expressing fusion proteins comprising epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an agonist or antagonist protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J Virol* 66:2).

The Multiple Antigen Peptide system for peptide-based immunization can also be utilized to generate an immunogen, wherein a desired portion of a polypeptide is obtained directly from organo-chemical synthesis of the peptide onto an oligomeric branching lysine core (see, for example, Posnett et al. (1988) *JBC* 263:1719 and Nardelli et al. (1992) *J Immunol.* 148:914). Antigenic determinants of proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the polypeptides of the present invention. For example, agonist or antagonist polypeptides can be generated as glutathione-S-transferase (GST-fusion) proteins. Such GST-fusion proteins can enable easy purification of the agonist or antagonist polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

4.5 Antisense, Ribozyme and Triplex Therapeutics

Another aspect of the invention relates to nucleic acids that are effective antisense, ribozyme and triplex antagonists of mutant or otherwise defective (e.g overexpressed) HNF nucleic acids or genes that are up- or down-regulated by an HNF polypeptide and or that contain an HNF binding site in their promoter region. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a functional HNF protein a gene that is up- or down-regulated by an HNF polypeptide and/or that contains an HNF binding site in its promoter region. Alternatively, the antisense construct is an oligonucleotide probe which is generated ex vivo and which, when introduced into the cell causes inhibition of expression by hybridizing with the mRNA and/or genomic sequences of an HNF gene that is up- or down-regulated by an HNF polypeptide and or that contains an HNF binding site in its promoter region. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the HNF nucleotide sequence of interest or gene that is up- or down-regulated by an HNF polypeptide and or that contains an HNF binding site in its promoter region, are preferred.

Antisense approaches involve the design of oligonucleotides (either DNA or RNA) that are complementary to HNF mRNA or mRNA of gene that is up- or down-regulated by an HNF polypeptide and or that contains an HNF binding site in its promoter region. The antisense oligonucleotides will bind to the mRNA transcript (e.g. a mutant transcript) and prevent translation. Absolute complementarity, although preferred, is not required a sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. *Nature* 372:333). Therefore, oligonucleotides complementary to either the 5' or 3' untranslated, non-coding regions of an HNF gene or gene that is up- or down-regulated by an HNF polypeptide and or that contains an HNF binding site in its promoter region could be used in an antisense approach to inhibit translation of endogenous HNF mRNA mRNA of a gene that is up- or down-regulated by an HNF polypeptide and or that contains an HNF binding site in its promoter region. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of an mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3 -(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the coding region sequence could be used, those complementary to the transcribed untranslated region are most preferred.

The antisense molecules should be delivered to cells which express the gene encoding the agonist or antagonist in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcript and thereby prevent translation of the mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpes virus vectors may be used), in which case administration may be accomplished by another route (e.g., systematically).

Ribozyme molecules designed to catalytically cleave mRNA transcripts can also be used to prevent translation of mRNA and expression of functional protein. (See, e.g., PCT International Publication WO90/11364, published Oct. 4, 1990; Sarver et al., 1990, Science 247:1222–1225). While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are hundreds of potential hammerhead ribozyme cleavage sites within the nucleotide sequence of a human HNF cDNA or cDNA of a gene that is up- or down-regulated by an HNF polypeptide and or that contains an HNF binding site in its promoter region. Preferably the ribozyme is engineered so that the cleavage recognition site is located near the 5' end of the mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a gene.

As in the antisense approach, the ribozymes can be composed of modified oligonucleotides (e.g. for improved stability, targeting, etc.) and should be delivered to cells which express the gene in vivo e.g., hypothalamus and/or the choroid plexus. A preferred method of delivery involves using a DNA construct "encoding" the ribozyme under the control of a strong constitutive pol III or pol II promoter, so that transfected cells will produce sufficient quantities of the ribozyme to destroy endogenous HNF messages and inhibit translation. Because ribozymes unlike antisense molecules, are catalytic, a lower intracellular concentration is required for efficiency.

Endogenous mutant HNF gene expression can also be reduced by inactivating or "knocking out" the HNF gene or its promoter using targeted homologous recombination. (e.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a wildtype, functional HNF (or a completely unrelated DNA sequence) flanked by DNA homologous to the endogenous mutant HNF gene (either the coding regions or regulatory regions of the HNF gene) can be used, with or without a selectable marker and/or a negative selectable marker, to transfect cells that express mutant HNF in vivo. Insertion of the DNA construct, via targeted homologous recombination, results in inactivation of the mutant HNF gene. Such approaches are particularly suited for generating transgenic animals, where modifications to ES (embryonic stem) cells can be used to generate animal offspring with an inactive HNF e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous (mutant or wildtype) gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C. 1991, Anticancer Drug Des., 6(6):569–84; Helene, C., et al., 1992, Ann. N.Y. Accad. Sci., 660:27–36; and Maher, L. J., 1992, Bioassays 14(12):807–15).

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding agonist or antagonist proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5–'3', 3'–4' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.6 Antibody Therapeutics

Another aspect of the invention pertains to antibodies or antigen binding agents, which are specifically reactive with an HNF protein or a protein encoded by a gene that is up- or down-regulated by an HNF polypeptide and/or that contains an HNF binding site in its promoter region. For example, by using immunogens derived from an HNF protein or a protein encoded by a gene that is up- or down-regulated by an HNF polypeptide and or that contains an HNF binding site in its promoter region, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide. Techniques for conferring immunogenicity on a protein or peptide include conjugation to carriers or other techniques well known in the art. An immunogenic portion of an agonist or antagonistprotein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an HNF protein of a mammal, e.g. antigenic determinants of a protein represented in Bach, I. et al., (1990) *Genomics* 8:155–164 or closely related homologs (e.g. at least 92% homologous, and more preferably at least 94% homologous).

Following immunization of an animal with an antigenic preparation of an agonist or antagonist polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256:495–497), the human B cell hybridoma technique (Kozbar et al., (1983) *Immunology Today*, 4:72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with an agonist or antagonist polypeptide of the present invention and monoclonal antibodies isolated from a culture comprising such hybridoma cells. In one embodiment anti-human antibodies specifically react with the HNF protein encoded by the DNA of ATCC deposit 97787.

The term antibody as used herein is intended to include fragments thereof which are also specifically reactive with one of the subject agonist or antagonist polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a protein conferred by at least one CDR region of the antibody.

Antibodies which specifically bind agonist or antagonist epitopes can also be used in immunohistochemical staining of tissue samples in order to evaluate the abundance and pattern of expression of each of the subject agonist or antagonist polypeptides. Anti-agonist or antagonist antibodies can be used diagnostically in immuno-precipitation and immuno-blotting to detect and evaluate protein levels in tissue as part of a clinical testing procedure. For instance, such measurements can be useful in predictive valuations of the onset or progression of proliferative disorders. Likewise, the ability to monitor protein levels in an individual can allow determination of the efficacy of a given treatment regimen for an individual afflicted with such a disorder. The level of polypeptides may be measured from cells in bodily fluid, such as in samples of cerebral spinal fluid or amniotic fluid, or can be measured in tissue, such as produced by biopsy. Diagnostic assays using anti-HNF antibodies can include, for example, immunoassays designed to aid in early diagnosis of diabetes.

Another application of antibodies of the present invention is in the immunological screening of cDNA libraries constructed in expression vectors such as λ gt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an agonist or antagonist protein, e.g. other orthologs of a particular HNF protein or other paralogs from the same species, can then be detected with antibodies, as, for example, reacting nitrocellulose filters lifted from infected plates with antibodies. Positive phage detected by this assay can then be isolated from the infected plate. Thus, the presence of HNF homologs can be detected and cloned from other animals, as can alternate isoforms (including splicing variants) from humans.

4.7 Methods of Treating Disease

A pharmaceutical composition of the present invention can be, as appropriate, any of the preparations described above, including isolated polypeptides, gene therapy constructs, antisense, ribozyme or triplex molecules, peptidomimetics or agents (e.g. small molecules), e.g. as identified in the drug assays provided herein.

Therefore, in one aspect, the invention features compounds that are agonists of a normal (functional) HNF bioactivity or of a normal (functional) bioactivity encoded by a gene that is up- or down-regulated by an HNF or that contains an HNF binding site in its promoter region. For example, to ameliorate disease symptoms involving insufficient expression of a gene and/or an inadequate amount of a functional protein in a subject, a gene therapeutic or a protein therapeutic can be administered to the subject. Alternatively, an agent (e.g. strong promoter) that upregulates the expression of a subject's endogenous, functional gene can provide a useful therapeutic.

In another preferred embodiment, the pharmaceutical composition is comprised of an antagonists of a disease causing (e.g. mutant) HNF bioactivity or of a normal (functional) bioactivity encoded by a gene that is up- or down-regulated by an HNF or that contains an HNF binding site in its promoter region. For example, to ameliorate disease symptoms involving expression of a mutant gene or overexpression of a normal gene in a subject, a therapeutically effective amount of an antisense, ribozyme or triple helix molecule to reduce or prevent gene expression, as described herein, may be administered to the subject. Alternatively, to ameliorate disease symptoms involving regulation via a protein of an upstream or downstream element in a biochemical pathway (e.g. initiation or regulation of gene transcription), a therapeutically effective amount of an antagonist compound (e.g. small molecule, peptide, or peptidomimetic) that can prevent binding of the wildtype protein to the nucleic acid, can induce a therapeutic effect. Further, to ameliorate disease symptoms involving a mutant (nonfunctional) protein, a therapeutically effective amount of an antibody, as described herein, may be administered to the subject. Preferably the antibody is administered in a delivery complex or in conjunction with an agent that allows entry of the antibody into cell nuclei.

Compounds as described above can be administered to a subject at a therapeutically effective dose to treat or ameliorate diabetes.

4.7.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.7.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91:3054–3057). A gene, or fragment thereof can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.8 Diagnostic and Prognostic Assays

In addition, the invention features probes and primers for use in a prognostic or diagnostic assay. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of: i) a sense or anti-sense sequence of HNF nucleic acid sequence; ii) a sense or anti-sense sequence of a gene that is up- or down-regulated by an HNF nucleic acid sequence or protein; or iii) a sense or anti-sense sequence of a gene that contains an HNF binding site in its promoter region, including 5' and/or 3' untranslated regions or each of the aforementioned genes. Particularly preferred primer sets for use in the disclosed diagnostic methods are set forth herein as SEQ. ID. Nos. 7 and 8; 9 and 10; 11 and 12; 13 and 14; 15 and 16; 17 and 18; 19 and 20; 21 and 22; 23 and 24; 25 and 26; and 27 and 28.

Although the following examples describe the identification of certain mutations in affected, but not non-affected human subjects, in type II diabetes families, based on the teachings set forth herein, one of skill in the art can readily identify additional mutations that result in type II diabetes. Detection of all such mutations are encompassed by the specification and claims.

In preferred embodiments, a probe further comprises a label group attached thereto and able to be detected, e.g. the label group is selected from amongst radioisotopes, fluorescent compounds, enzymes, and enzyme co-factors.

The present invention also provides methods for determining whether a subject is at risk for developing Type II diabetes. In preferred embodiments, the methods can be characterized as comprising detecting, in a sample of cells from the subject, the presence or absence of a genetic lesion characterized by at least one of (i) an alteration affecting the integrity of a gene encoding a protein, or a protein that is encoded by a gene that is up- or down-regulated by an HNF protein or a gene that contains an HNF binding site in its promoter region, or (ii) the mis-expression of an HNF gene encoding an HNF protein, or a protein encoded by a gene that is up- or down-regulated by an HNF gene or a gene that contains an HNF binding site in its promoter region.

To illustrate, such genetic lesions can be detected by ascertaining the existence of at least one of (i) a deletion of one or more nucleotides from an HNF gene, or a gene that is up- or down-regulated by an HNF nucleic acid sequence or protein, or a gene that contains an HNF binding site in its promoter region, (ii) an addition of one or more nucleotides to an HNF gene, or a gene that is up- or down-regulated by an HNF nucleic acid sequence or protein, or a gene that contains an HNF binding site in its promoter region, (iii) a substitution of one or more nucleotides to an HNF gene, or a gene that is up- or down-regulated by an HNF nucleic acid sequence or protein, or a gene that contains an HNF binding site in its promoter region, (iv) a gross chromosomal rearrangement of an HNF gene, or a gene that is up- or down-regulated by an HNF nucleic acid sequence or protein, or a gene that contains an HNF binding site in its promoter region, (v) a gross alteration in the level of a messenger RNA transcript of an HNF gene, or a gene that is up- or down-regulated by an HNF nucleic acid sequence or protein, or a gene that contains an HNF binding site in its promoter region, (vii) aberrant modification of an HNF gene, or a gene that is up- or down-regulated by an HNF nucleic acid sequence or protein, or a gene that contains an HNF binding site in its promoter region, such as of the methylation pattern of the genomic DNA, (vii) the presence of a non-wild type splicing pattern of a messenger RNA transcript of an HNF gene, or a gene that is up- or down-regulated by an HNF nucleic acid sequence or protein, or a gene that contains an HNF binding site in its promoter region, (viii) a non-wild type level of an HNF protein, or a protein encoded by a gene that is up- or down-regulated by an HNF nucleic acid sequence or protein, or a protein encoded by a gene that contains an HNF binding site in its promoter region, (ix) allelic loss of an HNF gene, or a gene that is up- or down-regulated by an HNF nucleic acid sequence or protein, or a gene that contains an HNF binding site in its promoter region, and (x) inappropriate post-translational modification of an HNF protein, or a protein that is encoded by a gene that is up- or down-regulated by an HNF nucleic acid sequence or protein, or a protein that is encoded by a gene that contains an HNF binding site in its promoter region. As set out below, the present invention provides a large number of assay techniques for detecting lesions, indicative of a predisposition to the development of or the existence of type II diabetes.

In an exemplary embodiment, there is provided a nucleic acid composition comprising a (purified) oligonucleotide probe including a region of nucleotide sequence which is capable of hybridizing to a sense or antisense sequence of: i) an HNF gene; ii) a gene that is up- or down-regulated by an HNF gene; iii) a gene that contains an HNF binding site in its promoter region or naturally occurring mutants thereof, or 5' or 3' flanking sequences or intronic sequences naturally associated with the subject genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) Science 241:1077–1080; and Nakazawa et al. (1994) PNAS 91:360–364), the latter of which can be particularly useful for detecting point mutations (see Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a target gene or a gene that is up- or down-regulated by an HNF nucleic acid sequence or protein, or a gene that contains an HNF binding site in its promoter region, under conditions such that hybridization and amplification of the gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in a gene from a sample cell are identified by alterations in restriction enzyme cleavage patterns. For example, sample and control DNA is isolated, amplified (optionally), digested with one or more restriction endonuclease, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the gene and detect mutations by comparing the sequence of the sample gene with the corresponding wild-type or mutant (control) sequence. Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). It is also contemplated that any of a variety of automated sequencing procedures may be utilized when performing the subject assays (Biotechniques (1995) 19:448), including sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type HNF sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an HNF sequence, e.g., a wild-type HNF sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control HNF nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol Cell Probes* 6:1). It is anticipated that in certain embodiments amplification may also be performed using Taq ligase for amplification (Barany (1991) *Proc. Natl Acad. Sci USA* 88:189). In such cases, ligation will occur only if there is a perfect match at the 3' end of the 5' sequence making it possible to detect the presence of a known mutation at a specific site by looking for the presence or absence of amplification.

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Another embodiment of the invention provides for a nucleic acid composition comprising a (purified) oligonucleotide probe including a region of nucleotide sequence which is capable of hybridizing to a sense or antisense sequence of a gene or a gene that is up- or down-regulated by an HNF nucleic acid sequence or protein, or a gene that contains an HNF binding site in its promoter region, or naturally occurring mutants thereof, or 5' or 3' flanking sequences or intronic sequences naturally associated with the subject genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, type II diabetes.

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of diabetes.

Any cell type or tissue, preferably hepatocytes, in which the target gene is expressed may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant proteins, or proteins encoded by a gene that is up- or down-regulated by an nucleic acid sequence or protein, or a protein encoded by a gene that contains an binding site in its promoter region, which are discussed, above, may also be used in disease diagnostics and prognostics. Such diagnostic methods, may be used to detect abnormalities in the level of protein expression, or abnormalities in the structure and/or tissue, cellular, or subcellular location of a protein. Structural differences may include, for example, differences in the size, electronegativity, or antigenicity of the mutant protein relative to the normal protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of*

Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product can be used to monitor the course of treatment or therapy.

4.9.1 Cell-free in vitro assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements.

Accordingly, in an exemplary screening assay of the present invention, the compound of interest is contacted with a protein which may function upstream (including both activators (enhancers) and repressors of its activity) or to proteins and/or nucleic acids (e.g. promoter) which may function downstream of the HNF polypeptide, whether they are positively or negatively regulated by it. To the mixture of the compound and the upstream or downstream element is then added a composition containing an HNF polypeptide. Detection and quantification of complexes of HNF with it's upstream or downstream elements provide a means for determining a compound's efficacy at antagonizing (inhibiting) or agonizing (potentiating) complex formation between an HNF and an HNF binding element (e.g. protein or nucleic acid). The efficacy of the compound can be assessed by generating dose response curves from data obtained using various concentrations of the test compound. Moreover, a control assay can also be performed to provide a baseline for comparison. In the control assay, isolated and purified HNF polypeptide is added to a composition containing the HNF binding element, and the formation of a complex is quantitated in the absence of the test compound.

Complex formation between the HNF polypeptide and a binding element may be detected by a variety of techniques. Modulation of the formation of complexes can be quantitated using, for example, detectably labeled proteins such as radiolabeled, fluorescently labeled, or enzymatically labeled HNF polypeptides, by immunoassay, or by chromatographic detection.

Typically, it will be desirable to immobilize either HNF or its binding protein to facilitate separation of complexes from uncomplexed forms of one or both of the proteins, as well as to accommodate automation of the assay. Binding of HNF to an upstream or downstream element, in the presence or absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/HNF (GST/HNF) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conductive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of HNF-binding protein found in the bead fraction quantitated from the gel using standard electrophoretic techniques.

Other techniques for immobilizing proteins on matrices are also available for use in the subject assay. For instance, an HNF protein or its cognate binding protein can be immobilized utilizing conjugation of biotin and streptavidin. For instance, biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with HNF or with a protein encoded by a gene that is up- or down-regulated by HNF or a protein that is encoded by a gene that contains an HNF binding site, but which does not interfere with binding of upstream or downstream elements can be derivatized to the wells of the plate, and protein trapped in the wells by antibody conjugation. As above, preparations of a binding protein and a test compound are incubated in the protein presenting wells of the plate, and the amount of complex trapped in the well can be quantitated. Exemplary methods for detecting such complexes, in addition to those described above for the GST-immobilized complexes, include immunodetection of complexes using antibodies reactive with the protein binding element, or which are reactive with the HNF protein or protein that is encoded by a gene that contains an HNF binding site and competes with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the binding partner. To illustrate, the binding partner can be chemically cross-linked or genetically fused with horseradish peroxidase, and the amount of polypeptide trapped in the complex can be assessed with a chromogenic substrate of the enzyme, e.g. 3,3'-diaminobenzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein can be used. Alternatively, the protein to be detected in the complex can be "epitope tagged" in the form of a fusion protein which includes, in addition to the HNF sequence or sequence of a gene that is up- or down-regulated by HNF or that contains an HNF binding site, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.). Transcription factor-DNA binding assays are described in U.S. Pat. No. 5,563,036, which is owned by Tularik and is specifically incorporated by reference herein. in vitro DNA binding assays are also described in further detail in the following examples.

Further, an in vitro transcriptional control assay can be used to detect compounds which can be used for treatment of diabetes. For example, cells can be engineered to express HNF genes and a second gene construct containing an HNF response element in operative linkage with a reporter gene construct, such as luciferase or chloramphenicol acetyl transferase, or other reporter gene known in the art. Cells can then be contacted with test compounds. HNF ligands will cause transcriptional activation of the reporter gene as compared to that seen in control cells in the absence of ligand or in the absence of the recombinant HNF or HNF response element-reporter gene construct. For testing antagonist compounds, cells can be contacted with an agonist prior to being contacted with test compounds and an inhibition of reporter gene transcription or product can be detected. An exemplary in vitro transcription assay is described in further detail in the following examples.

Also, a DNA footprinting assay can be used to detect agonists or antagonists of HNF for the treatment of diabetes. For example, DNase I footprinting may be used to detect compounds which alter the binding of an HNF protein to nucleic acids (see for example, Zhong et al. 1994. Mol. Cell Biol. 14:7276).

Further, HNF may be translationally or post-translationally modified by processes such as mRNA editing or protein truncation. Assays to specifically monitor these processes can be performed according to protocols, which are well-known in the art.

4.9.2. Cell based assays

In addition to cell-free assays, such as described above, the HNF proteins provided by the present invention also facilitates the generation of cell-based assays for identifying small molecule agonists/antagonists and the like. For example, cells can be caused to overexpress a recombinant HNF protein in the presence and absence of a test agent of interest, with the assay scoring for modulation in HNF responses by the target cell mediated by the test agent. As with the cell-free assays, agents which produce a statistically significant change in HNF-dependent responses (either inhibition or potentiation) can be identified. In an illustrative embodiment, the expression or activity of an HNF is modulated in embryos or cells and the effects of compounds of interest on the readout of interest (such as initiation of transcription) are measured. For example, the expression of genes which are up- or down-regulated in response to an HNF dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Exemplary cell lines may include hepatocyte cell lines. Further, the transgenic animals discussed herein may be used to generate cell lines, containing one or more cell types involved in type II diabetes, that can be used as cell culture models for this disorder. While primary cultures may be utilized, the generation of continuous cell lines is preferred. For examples of techniques which may be used to derive a continuous cell line from the transgenic animals, see Small et al., 1985, Mol. Cell Biol. 5:642–648.

For example, the effect of a test compound on a variety of end points could be tested. Similarly, hepatocyte cells can be treated with test compounds or transfected with genetically engineered HNF genes. The hepatocyte cells can then be examined for phenotypes associated with diabetes, including, but not limited to changes in insulin level and/or glucose tolerance.

In the event that the HNF proteins themselves, or in complexes with other proteins, are capable of binding DNA and modifying transcription of a gene, a transcriptional based assay could be used, for example, in which an HNF responsive regulatory sequence is operably linked to a detectable marker gene.

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject HNF polypeptides can be used in a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with an HNF(e.g., HNF binding proteins" or "HNFbp").

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for an HNF polypeptide. The second hybrid protein encodes a transcriptional activation domain fused in frame to a sample gene from a cDNA library. If the bait and sample hybrid proteins are able to interact, e.g., form an HNF dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the HNF and sample proteins. An exemplary tissue culture based reporter assay is described in further detail in the following Examples.

4.10 Transgenic animals

These systems may be used in a variety of applications. For example, the cell- and animal-based model systems may be used to further characterize HNF genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

4.10.1. Animal-based systems

One aspect of the present invention concerns transgenic animals which are comprised of cells (of that animal) which contain a transgene of the present invention and which preferably (though optionally) express an exogenous HNF protein in one or more cells in the animal. An HNF transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of an HNF protein can be essential for many forms of lineage analysis and can additionally provide a means to assess the effects of, for example, lack of HNF expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject HNF proteins. For example, excision of a target sequence which interferes with the expression of a recombinant HNF gene, such as one which encodes an antagonistic homolog or an antisense transcript, can be designed to activate expression of that gene. This interference with expression of the protein can result from a variety of mechanisms, such as spatial separation of the HNF gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant HNF protein can be regulated via control of recombinase expression.

Use of the crelloxP recombinase system to regulate expression of a recombinant HNF protein requires the construction of a transgenic animal containing transgenes encoding both the Cre recombinase and the subject protein. Animals containing both the Cre recombinase and a recombinant HNF gene can be provided through the construction of "double" transgenic animals. A convenient method for providing such animals is to mate two transgenic animals each containing a transgene, e.g., an HNF gene and recombinase gene.

One advantage derived from initially constructing transgenic animals containing an HNF transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic HNF transgene is silent will allow the study of progeny from that founder in which disruption of HNF mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the HNF transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, an HNF transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of an HNF protein (either agonistic or antagonistic), and antisense transcript, or an HNF mutant. Further, in such embodiments, the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83:9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting an HNF gene of interest in ES cells, these changes can be introduced into the germlines of animals to generate chimeras. The gene targeting procedure is accomplished by introducing into tissue culture cells a DNA targeting construct that includes a segment homologous to a target HNF locus, and which also includes an intended sequence modification to the HNF genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting an HNF gene function through the use of a targeting transgene construct designed to undergo homologous recombination with one or more HNF1 genomic sequences. The targeting construct can be arranged so that, upon recombination with an element of an HNF gene, a positive selection marker is inserted into (or replaces) coding sequences of the targeted gene. The inserted sequence functionally disrupts the HNF gene, while also providing a positive selection trait. Exemplary HNF targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the HNF coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the HNF gene knocked out in various tissues of the offspring by probing the Western blot with an antibody against the particular HNF protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of an HNF gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*; (Cold Spring Harbor Laboratory Press, Cold Spring Harbor, N.Y., 1986).

5. EXAMPLES

5.1 Genetic Mapping of a Diabetes Gene

A human gene implicated in MODY had been previously mapped to a 7 cM region of chromosome 12q between marker D12S86 and D12S342 by Vaxillaire et al., (Vaxillaire, M. et al., (1995) *Nature Genetics* 9:418–423). S. Menzel et al., further localized the gene to a 5 cM region between D12S86 and D12S807/D12S820. On average 5 cM corresponds to approximately 5 megabases in the human genome (encoding on average somewhere between 50 and 100 genes). This level of resolution is unsatisfactory for gene identification. Further, this region of chromosome 12q was not sufficiently characterized so as to be certain of the exact marker location or order.

By genetically analyzing type II diabetes families, the order of markers in the interval was refined; and the interval between AFMa82za5 and AFM1 65yb12 was narrowed to about 2.5 cM, corresponding to approximately 2.5 megabases (encoding on average about 25–50 genes). Typically the goal of human genetics is to refine the location of a gene to within about a 0.5 cM interval.

5.2 Physical Mapping of a Diabetes Gene

Simultaneous with the human genetic approach described above in section 5.1, a high resolution "sequence ready" physical map of the regions of interest was created. Generating a physical map involved isolating DNA clones that span the genetic interval defined by the markers described above (AFMa82za5 and AFM165yb12).

YAC (yeast artificial chromosomes) maps were constructed using the publicly available markers in the region in an attempt to confirm the order of published YACs and markers. The YAC libraries were screened by PCR amplification of a DNA pool representing the libraries. (A description of the screening protocol can be found in Research Genetics Catalog #95001). Once the YAC map was assembled, a bubble vectorette and interspersing repeat sequence (IRS) were used to both clone the ends of the YACs and generate more markers throughout the region (*Current Protocols in Human Genetics First Edition*, (1994) John Wiley & Co., N.C. Dracopoli et al., eds). Primers were designed from these sequences and used to rescreen the YAC library by PCR to identify adjacent YACs.

In order to further aid in gene identification and to confirm the integrity of the YAC contig and marker order, BACs (bacterial artificial chromosome) and PACs (P1 artificial chromosomes) clones were isolated. The same STSs (sequence tag sites, used for PCR) used to construct the YAC contig were used to screen the Research Genetics human BAC library (Research Genetics, Huntsville, Ala.) and Genome Systems PAC library (Genome Systems) according to manufacturers' suggested screening protocols. Additional STSs were produced by cloning and sequencing the ends of the BAC and/or PACs. Random sequencing of BamHI/BglII restricted libraries of the BACs and PACs was also used to generate more STSs. Creation of over 400 PCR markers enabled the creation of a high resolution sequence ready physical map consisting of a minimal tiling path of 23 BAC and PAC clones with markers spaced approximately every 5 kb. The BAC and PAC that make up the minimal tiling path were sized by pulse gel electrophoresis and range in size from 40 to 230 kb. Sizing all the clones in the interval between the markers AFMa82za5 and GGAT1E2 determined the size of the region to be approximately 2.4 Mb.

5.3 Identification of the Diabetes Gene

Simultaneous with the human genetic approach described above in section 5.1 and the physical mapping described above in section 5.2, the following techniques were employed to identify specific genes in the target region of chromosome 12q: i) sample (shotgun) sequencing; ii) exon trapping; iii) cDNA selection; and iv) transcription mapping. A brief description of each technique is provided below.

Materials and Methods

Sample (shotgun) sequencing

Random sheared libraries were made from all the BAC and PAC clones within the defined genetic interval by sonicating the DNA. Fragments in the size range of 3–5 kb were cloned into the vector pCDNAII (Invitrogen, San Diego, Calif.). Approximately 4000 subclones were sequenced with vector primers in order to generate 8-fold sequence coverage of each BAC or PAC clone. All sequences were processed through an automated sequence analysis pipeline that assessed quality, removed vector sequences, masked repetitive sequences. The sequences that passed through the automated sequence analysis pipeline were then aligned to public DNA and protein databases using BLAST algorithms (Altschul et al., 1990). Both known and novel genes were identified in the relevant region between markers AFMa82za5 and GGAT1E2 on chromosome 12.

Exon trapping

Exon trapping was carried out by isolating internal exons from individual P1 and BAC clones carrying genomic DNA using the exon trapping vector D-pSPL3 as described in the Gibco BRL Exon Trapping System Instruction Manual (Cat. No. 18449-017). In this system, exons are trapped from genomic DNA subcloned into D-pSPL3 as a result of the interaction between vector splice sites and splice sites flanking exons in the genomic DNA. D-pSPL3 was derived from the splicing vector pSPL3 (Gibco BRL) by deletion of the NdeI (1119)-NheI (1976) fragment in the HIV tat intron to eliminate the cryptic splice-donor site at position 1134 in the pSPL3 sequence.

Briefly, the exon trapping procedure involves: subcloning the P1/Bac clone into D-pSPL3, plating of the resulting D-pSPL3 library and preparation of DNA, transfection of library DNA into COS-7 cells, RNA isolation after transient expression, first strand cDNA synthesis using a vector-specific primer by reverse transcriptase polymerase chain reaction (RT-PCR), cDNA amplification by an initial round of PCR, BstXI digestion of primary PCR products to eliminate vector-vector and cryptic splicing products, secondary amplification with dUMP-containing primers, and cloning of secondary PCR products into the phagemid vector pAMP10 (Gibco BRL) using uracil DNA glycosylase (UDG).

P1/BAC DNA was prepared from overnight cultures (1000 ml LB/kanamycin 25 µg/ml) by alkaline lysis, treated with RNase A, purified by phenol/chloroform/isoamyl alcohol (25:24:1) extraction, ethanol precipitated, rinsed in 70% ethanol, dried and resuspended in 400 µl deionized water. 5–10 µg P1/Bac DNA was cut with either BamHI and BglII, or PstI, as specified by the manufacturer (New England Biolabs). The digested DNA was phenol extracted, ethanol precipitated, and resuspended in 50 µl deionized water.

Stocks of BamHI-cut and PstI-cut D-pSPL3 DNA were prepared by digesting 50–100 µg DNA with the corresponding enzyme and dephosphorylating the linearized vector with calf intestine alkaline phosphatase as specified by the manufacturers (New England Biolabs and Boehringer Mannheim, respectively). The linearized vector was purified away from uncut plasmid DNA by agarose gel electrophoresis and electroelution and assayed to assess the level of uncut and self-ligated vector as described elsewhere (Pulido and Duyk. In *Current Protocols in Human Genetics First Edition*, (1994) John Wiley & Co., N.C. Dracopoli et al., eds).

Insert-vector ligation reactions contained 200 ng vector DNA, 20 ng insert DNA, 4 µl of 5× ligation buffer (Gibco BRL), and 0.6 units of T4 DNA ligase (Gibco BRL) in a total volume of 20 µl, and were incubated for 1–2 hours at room temperature. 2 µl of the ligation reaction was transformed into *Escherichia coli* XL-1B cells (New England Biolabs) by electroporation (Bio-Rad Instruction Manual Cat. No. 165-2098). Routinely, 0.1 and 0.01 ml of each transformation was plated on LB/carbenicillin (100 µg/ml) plates to obtain the library titer. For each library, plasmid DNA from at least 20 single transformants was restriction digested to assess the efficiency of the shotgun subcloning, and sequenced. The sequencing primers were: SPL3A (forward primer; 5'-CAT GCT CCT TGG GAT GT -3'; SEQ ID NO. 1 Operon Technologies) and SPL3C (reverse primer; 5'-TGA GGA TTG CTT AAA GA-3'; SEQ ID NO.2; Operon Technologies).

Each P1/BAC library was plated on three 150-mm LB/carbenicillin plates at a density of 7×10³ colonies/plate (for a total of 2.1×10⁴ colonies) and grown overnight at 370° C. The colonies were resuspended and pooled in a total of 20 ml LB medium. DNA was prepared from the pooled cell suspension using a Qiagen-tip 500 column as specified by the manufacturer (Qiagen Plasmid Handbook).

Transient transfections of COS-7 cells (American Type Culture Collection) were performed in 3.5-cm 6-well dishes using LipofectACE reagent (Gibco BRL) as described in the Gibco BRL Exon Trapping System Instruction Manual (Cat. No. 18449-017). The cells were passaged one day prior to transfection by placing 4×10⁵ cells in 2 ml supplemented D-MEM into each well. 1–3 µg DNA mixed with 5 µl LipofectACE reagent in 1 ml Opti-MEM medium was added per well. In addition to P1/Bac library DNA, every round of transfections included as controls: D-pSPL3 DNA, the Gibco BRL exon control plasmid, and a "no DNA" transfection. After a 5-hour incubation, the lipid-DNA complexes were removed, and the cells were added 2 ml supplemented D-MEM and incubated for 24 hours.

Total RNA from transiently transfected COS-7 cells was isolated using TRIzol reagent (Gibco BRL) as described in the Gibco BRL Exon Trapping System Instruction Manual (Cat. No. 18449-017).

The reverse transcriptase polymerase chain reaction (RT-PCR) was performed as described in the Gibco BRL Exon Trapping System Instruction Manual (Cat. No. 18449-017) and contained in a total volume of 20 µl: 3 µg total RNA, 1 µl of 20 µM oligonucleotide SA2 (5'-ATC TCA GTG GTA TTT GTG AGC-3'; SEQ ID NO. 3 [Gibco BRL]), 4 µl of 5× first strand buffer, 2 µl of 0.1M DTT, 1 µl of 10 mM dNTP mix (10 mM each dATP, dTTP, dCTP, dGTP), 1 μl of SuperScript II Reverse Transcriptase (Gibco BRL), and DEPC-treated water to a final volume of 20 μl. Following RT-PCR, the RNA template was degraded by addition of 1 μl RNase H (Gibco BRL) and incubation for 10 min at 550° C.

The primary PCR reaction contained in a total volume of 40 μl: 8 μl of RT-PCR mixture, 2 μl of 20 μM oligonucleotide SA2.2 μl of 20 μM oligonucleotide SD6 (5=-TCT GAG TCA CCT GGA CAA CC-3'; SEQ ID NO. 4 [Gibco BRL]), 0.8 μl of 10 mM dNTP mix, 4 μl of 10×GeneAmp PCR buffer (Perkin Elmer) and 22.7 μl deionized water. The mixture was overlaid with 50 μl mineral oil, placed in a Perkin Elmer Cetus 480 thermal cycler preheated to 94° C., and incubated for 5 minutes. The temperature was reduced to 80° C., and 0.5 μl (2.5 units) of AmpliTaq DNA polymerase (Perkin Elmer) was added per tube. Six cycles of PCR amplification were performed as follows: 94° C. for 1 minute, 60° C. for 1 minute, and 72° C. for 5 minutes, with a final extension at 72° C. for 10 minutes.

10 μl of primary PCR reaction was removed (uncut primary PCR) and 2.5 μl (25 units) of BstXI (Gibco BRL) was added to the remaining reaction which was incubated at 55° C. overnight.

The secondary PCR reaction contained in a total volume of 50 μl: 5 μl of BstXI-treated primary PCR product, 1 μl of 20 μM secondary amplification primer mix [20 μM each dUSD2 (5'-CUA CUA CUA CUA GTG AAC TGC ACT GTG ACA AGC TGC-3' SEQ ID NO. 5 [Gibco BRL]) and dUSA4 (5'-CUA CUA CUA CUA CAC CTG AGG AGT GAA TTG GTC G-3'); SEQ ID NO. 6 [Gibco BRL]), 1 μl of 10 mM dNTP mix, 5 μl of 10×GeneAmp PCR buffer (Perkin Elmer), and 38 μl deionized water. The mixture was overlaid with 50 μl mineral oil, placed in a Perkin Elmer Cetus 480 thermal cycler preheated to 94° C., and incubated for 5 minutes. The temperature was reduced to 80° C., and 0.5 μl (2.5 units) of AmpliTaq DNA polymerase (Perkin Elmer) was added per tube. 30 cycles of PCR amplification were performed as follows: 94° C. for 1 minute, 60° C. for 1 minute, and 72° C. for 3 minutes, with a final extension at 72° C. for 10 minutes. As a control for the BstXI treatment, uncut primary PCR samples were amplified in parallel as described for BstXI-treated samples. The secondary PCR products were routinely analyzed by agarose gel electrophoresis (2% agarose).

The UDG cloning reaction contained: 6 μl of secondary PCR product, 2 μl of pAMP 10 cloning vector (Gibco BRL), 1 μl of 10×GeneAmp PCR buffer (Perkin Elmer), and 1 μl (1 unit) of uracil DNA glycosylase (Gibco BRL). The reaction was incubated at 37° C. for 30 minutes. 2 μl of the reaction was transformed into DH11S cells (Gibco BRL) by electroporation (Bio-Rad). Transformants were selected on LB/carbenicillin plates and evaluated by colony PCR. The colony PCR reaction contained in 25 μl total volume: colony resuspended in 10 μl deionized water, 0.5 μl of 20 μM secondary amplification primer mix (see above), 0.5 μl of 10 mM dNTP mix, 2.5 μl of 10×GeneAmp PCR buffer (Perkin Elmer), 0.25 μl (1.25 units) AmpliTaq DNA Polymerase (Perkin Elmer), and 11.3 μl deionized water. PCR reactions were performed in the Perkin-Elmer Cetus GeneAmp PCR System 9600. The amplification parameters were: 94° C. for 5 min, followed by 30 cycles of: 94° C. for 45 seconds, 55° C. for 30 seconds, and 72° C. for 1 minute, with a final extension at 72° C. for 10 minutes. The colony PCR products were analyzed in 2% agarose gels. Clones with insert sizes greater than 177 bp were sequenced using M13 forward and reverse primers.

cDNA selection cDNA selection or screening of arrayed genomic fragments was designed for isolating genes with diverse expression patterns from large genomic regions. Clones that make up the minimal tiling path of the critical region were hybridized with cDNA probes quantitatively depleted of repetitive sequences. cDNA probes were synthesized from the following human tissues: adult and fetal brain, adult and fetal liver, fibroblast, Cacao cells (immortalized colon cancer cells), skeletal muscle, placenta, testis, pancreas, pancreatic islets, Jurkat cells (a lymphoblas cell line) and prostate. The cDNA selection technique was carried out as described in Current Protocols in Human Genetics, N. Dracopoli et al., eds. Briefly, the radiolabeled cDNA probe was made by synthesizing first-strand cDNA by reverse transcription of mRNA isolated from the tissues described above. The first strand cDNA is used as a template to produce radiolabeled second-strand cDNA by random hexamer-primed synthesis. Highly repetitive sequences were removed from the radiolabeled probe by hybridization with DNA cellulose. Filters containing the BAC and PAC clones of the minimal tiling path were hybridized with the radiolabeled cDNA probes. The cDNA fragments that hybridized specifically were then cloned into the vector pAMP 10 (Life Technologies, Gaithersburg, Md.) with the enzyme uracil DNA glycosylase as described by the manufacturer (Life Technologies, Gaithersburg, Md.). Approximately 3000 clones were sequenced. These clones fell into 470 "bins"—meaning that they were part of the same gene. Out of these 470 bins, 131 were shown to overlap to genomic clones in the critical region by PCR with primers specific for the cDNA fragment selected. These clones were also confirmed to be transcripts by RT-PCR on tissues from which they arose. Another 134 bins require confirmation. Still another 205 sequences were not followed, because they were shown to contain either repetitive sequences and/or made up of only polyA tracks.

Results

The combination of sample sequencing, exon-trapping and cDNA selection allowed the identification of over 100 transcripts. Many of the transcripts showed no sequence homology to sequences of genes published to date. A list of known human genes and homologues to known genes of non-human species is presented in the following Table 2.

TABLE 2

| # on map | Gene name |
| --- | --- |
| 1 | paxillin (cytoskeleton protein) |
| 2 | 60S acidic ribosomal protein |
| 3 | NDPK (tumor metastasis inhibitor nm 23) |
| 4 | acyl-coA dehydrogenase (ACADS) |
| 5 | novel gene #1 |
| 6 | novel gene #2 |
| 7 | ADP-ribosylation factor |
| 8 | HNF/transcrip. factor TCF1 |
| 9 | thyroid receptor interactor |
| 10 | novel gene #3 |
| 11 | novel gene #4 |
| 12 | cytosine-5 methyltransferase |
| 14 | 4-hydroxyphenylpyruvate dioxygenase |
| 15 | novel gene #5 |
| 16 | vacuolar protein sorting |
| 17 | human restin (cytoplasmic linker protein) |

DNA obtained from affected and non-affected individuals were analyzed for the presence of a mutation in any of the genes listed in Table 2. No mutations were found within the complete sequence of tumor metastasis inhibitor nm 23 or novel gene #2. In addition, although 30–50% of the other genes had been covered, no mutations were found However, as described in further detail in the following examples, mutations were found in regions of HNF1 from affecteds, but not non-affecteds.

5.4 The Diabetes Gene is Expressed in Pancreatic Islet Cells

RT-PCR with primers at the 5' end of the HNF1 gene was carried out to determine if the gene was expressed in pancreatic islets. 30 µg of total RNA were treated with DNAse-free RNAse (Boehringer Mannhiem, Indianapolis, Ind.) and incubated for 30 min. at 37° C. After incubation the product was treated with phenol/chloroform and ethanol precipitated. First-stand synthesis was carried out with 6 µg of DNAse-treated RNA, oligo dT and superscript reverse transcriptase (Life Technologies, Germantown, Md.). The second strand was synthesized with a primer unique to the gene with Vent polymerase (New England Biolab, Beverly, Mass.) to increase fidelity during synthesis. The results showed that the HNF1 gene is expressed in pancreatic islet cells.

Northerns containing RNA isolated from islets of affecteds and non-affected individuals was also carried out using a probe from the HNF-1 gene. No difference was observed between affected and non-affected individuals.

5.5 PCR Primers for Analyzing Mutations in the HNF1 Gene That Result in Type II Diabetes The following conditions were used to sequence the exons from affected and non-affected individuals in the hope of identifying a mutation. One set of PCR primers was designed for each of the first nine exons from intronic sequences obtained from the genomic clone (ATCC Designation No. 97787). Six set of primers were used to amplify the last exon (exon 10), since it was 1455 bp long. Each primer set designed was first tested on genomic DNA to confirm that it produced a specific PCR product and that the product amplified only on chromosome 12. PCR was carried out with the primer sets shown in Table 3.

The PCR reaction was carried out with 1xPCR buffer (1.5 mM MgCl$_2$, 50 mM KCl, 10mM Tris-HCl, pH 8.3 and 0.001% gelatin; Perkin Elmer, Foster City, Calif.); 250 mM of each of the four deoxynucleotide triphosphates (adenine, guanine, cytosine and thymine); 0.8 mM forward/reverse primers; 0.5 µ/ml Amplitaq polymerase (Perkin Elmer, Foster City, Calif.); and 20 ng of genomic DNA from affected and non-affected individuals. The PCR program was as follows 95#161#C, 1min; 35 cycles of 95#161#, 30#161#sec; 60#161#C, 30#161#sec; 72#161#C; 45 sec and finally 72#161#C, 10 min.

Removal of primer-dimer products was carried out before the samples were submitted for fluorescent sequencing. Removal of primer-dimer products was done in 1X Perkin Elmer PCR buffer and by adding 2 µ/ml Exonuclease I (Amersham, Arlington Heights, Ill.) and 0.04 µ/ml shrimp alkaline phosphatase (Amersham, Arlington Heights, Ill.). The sample was kept for 37#161#C, 30 min and the enzymes were inactivated for 80#161#C, 10 min. The end product of the reaction was quantified and 0.5–1 mg DNA for each sequencing reaction was submitted for sequencing. Six-fold sequencing was carried out for each exon to identify mutations.

TABLE 3

Exon sizes and primers

| Exon # | Exon Size | 5' end primer sequence | 3' end primer sequence |
|---|---|---|---|
| 1 | 348 | 5'CTCCAGGCACTGGGTGAG3' (SEQ. ID. NO.7) | 5'CTCCAGCTCTTTGAGGATGG3' (SEQ. ID. No. 8) |
| 2 | 200 | 5'GCAGATCCCGTCCTTGC3' (SEQ. ID No. 9) | 5'GTCANTACTTACGCTGCGCC3' (SEQ. ID. No. 10) |
| 3 | 187 | 5'GACGAGGGAAGGTGAGAGTG3' (SEQ. ID. No. 1) | 5'CCGTTGTACCTATTGCACTCC3' (SEQ. ID. No. 12) |
| 4 | 237 | 5'CAGCCTCAAACCCTCCG 3' (SEQ. ID. No. 13) | 5'CCAGGGGAGCTGTGAGC3' (SEQ. ID. No. 14) |
| 5 | 201 | 5'CAGGACACTGCTTCCCTCTC3' (SEQ. ID. No. 15) | 5'CTGCTCCAGTATCTCCCTGC3' (SEQ. ID. No. 16) |
| 6 | 206 | 5'AGCTGGTGAGTGTCCTTGCT3' (SEQ. ID. No. 17) | 5'ACCAGCTTACCGATGACCAG3' (SEQ. ID. No. 18) |
| 7 | 191 | 5'ATTAGTGGCAGGTCCCAGTG 3' (SEQ. ID. No. 19) | 5'ATCCATTGACAGCCAACCTC 3' (SEQ. ID. No. 20) |
| 8 | 123 | 5'TGTAATGGGGAGAGGGTCTG3' (SEQ. ID. No. 21) | 5'AGAGCAGCCTCCTGAGCC 3' (SEQ. ID. No. 22) |
| 9 | 145 | 5'CTCCCGCAGACTATGCTCAT 3' (SEQ. ID. No. 23) | 5'GCTGCAGGTGCTGGATG3' (SEQ. ID. No. 24) |
| 10 | 1445 | 5'TCCAGCTCCTCTTGTCACCT3' (SEQ. ID. No. 25) | 5'TCAGCAGAGCAAGAAAAGCA3' (SEQ. ID. No. 26) |

5.6 Identification of a Mutation in HNF1 That Results in Type II Diabetes

PCR primers using the following 5' end primer sequence (forward) and 3' primer sequence (reverse) was performed on DNA obtained from subjects affected with MODY and normal subjects:

| 5' end primer sequence | 3' end primer sequence |
|---|---|
| 5' GCAGATCCCGTCCTTGC 3' (SEQ. ID. No. 27) | 5' GTCATTACTTACGCTGCGCC 3' (SEQ. ID. No. 28) |

A 237 bp product was obtained. The sequence of the PCR product from type II diabetes patients were then obtained and compared with the PCR product obtained from normal (non-diabetic) subjects. Based on this analysis it was found that certain type II diabetes subjects contained a heterozygous point mutation in nucleotide 414 of hHNF1 (the wildtype sequence of which is shown in FIG. 2 of Bach, I. et al. (1990) *Genomics* 8:155–164) See FIG. 3. In these type II diabetic subjects, the wildtype C in one strand of DNA was changed to a T. Because the mutation is dominant, on the amino acid level, the basic amino acid arginine encoded by CGG in the normal wildtype, is mutated to the hydrophobic tryptophan.

5.7 Identification of Another Mutation in HNF1 That Results in Type II Diabetes PCR was performed on DNA obtained from a subject with type II diabetes using the exon 4 primers set forth in Table 3. The amplification product was sequenced and found to contain an insertion of a cytosine at position 895 relative to the wildtype sequence (See FIG. 4). An insertion of cytosine produces a frame shift downstream of the mutation and thereby changes the codon useage of the gene, so that a stop codon (TAA) occurs beginning at nucleotide 969 in the mutant sequence.

5.8 Tissue Culture Based Reporter Assays For Identifying Compounds that Modulate the Expression of a Gene or the Activity of a Gene Product Involved in Diabetes A heterologous system is constructed by adding the albumin promoter or a multimerized responsive segment of the albumin promoter, e.g. box B, (Schorpp, M. et al., (1988) *J Mol. Biol.* 202:307–320; Tronche, F. et al., (1989) Mol. Cell Biol. 9:4759–4766) to a reporter gene (e.g., luciferase, green fluorescent protein) according to standard procedures.

To identify antagonists of a mutant HNF1 bioactivity, the albumin promoter/reporter construct and HNF mutant gene are transfected into a cell line that expresses high levels of HNF1 and secretes albumin (e.g. differentiated hepatocyte cell lines, such as FAO or H411- Cereghini, S. et al., (1990) *EMBO J.* 9:2257–2263; Herbst, R. S. et al., (1991) *New Biol.* 3:289–296). The presence of the mutant HNF1 results in decreased expression from the albumin promoter, therefore the addition of a candidate compound that relieves the suppression caused by the HNF1 mutant results in increased albumin expression, which is detected by detecting the reporter gene. As a control for specificity, the same cell line is transfected with the HNF mutant gene and a promoter/reporter construct and contacted with the candidate antagonist, wherein the promoter does not respond to HNF1.

To identify agonists of a functional HNF1 bioactivity, the albumin promoter/reporter construct, described above, in conjunction with a functional (e.g. wildtype) HNF1 gene are transfected into a cell line that expresses low levels of HNF1 and that do not produce appreciable levels of albumin (dedifferentiated hepatocyte cell lines, such as C2 and H5; Cereghini, S. et al., (1 990) *EMBO J.* 9:2257–2263; Herbst, R. S. et al., (1991) *New Biol* 3:289–296). The presence of the HNF agonist results in increased expression from the albumin promoter, which is detected by detecting the reporter gene. Again, as a control for specificity, the same cell line is contacted with the HNF agonist and transfected with a promoter/reporter construct, wherein the promoter does not respond to HNF1.

5.9 In vitro Transcription Assays For Identifying Compounds that Modulate the Expression of a Gene or the Activity of a Gene Product Involved in Diabetes Hepatonuclear extracts are prepared according to the method of Gorski et al., (Gorski, K. et al., (1986) *Cell* 47:767–776). The in vitro transcription assay is essentially as described previously (Wanke, I. E. and N. C. W. Wong (1991) J. Biol. Chem. 266:6068–6072), except that 1.5 µg of a plasmid containing nucleotides −650 to +22 of the mouse albumin promoter (Wuarin, J. et al., (1990) J. Mol. Biol. 214:865–874) attached to a G-free cassette (GFC) of 320 nucleotides, pAlb-320 (Gorski, K. et al., (1986) *Cell* 47:767–776) and 0.3 µg of a plasmid containing nucleotides −404 to +10 of the adenovirus major late promoter fused to a 200-nucleotide GFC (pAd$_2$MLP-200) are used.

Compounds that modulate expression of the albumin gene without affecting expression from the adenovirus major late promoter are then identified and further tested for ability to agonize or antagonize HNF1.

5.10 In vitro DNA Binding Assays For Identifying Agonists or Antagonists of an HNF1 Bioactivity HNF1 can be partially purified from a hepatocyte extract by heparin-agarose or wheat germ agglutinin using standard procedures (Lichtsteiner, S. and U. Schibler (1989) Cell 57:1179–1187).

Partially purified or recombinant HNF1 is incubated with 25,000 cpm (20 fmol) of $^{32}$P-labeled blunt-ended probe (comprised of the albumin promoter or a segment thereof, such as box B) in a reaction mixture containing 10% sucrose, 3.75 mM HEPES, pH 7.6, 2.75 mM MgCl$_2$, 1.5 mM spermidine, 2 ng of poly (dI-dC), 100 ng of bovine serum albumin, and 75 ng of sonicated salmon sperm DNA at room temperature for at least 30 minutes, then separated by 5% nondenaturing polyacrylamide gel electrophoresis (PAGE) in 0.5 TBE buffer at 100V for at least 2.5 hours.

Contact of the mixture with an HNF1 agonist results in increased DNA binding, while contact with an antagonist results in decreased DNA binding. A negative control is provided by replacing the HNF1 and $^{32}$P-labeled blunt ended probe in the mixture described above, with a different transcription factor and a promoter containing a DNA binding site recognized by the different transcription factor. HNF1 agonists and antagonists affect the DNA binding of HNF 1, but not that of the control transcription factor.

5.11 In vitro Dimerization/Tetramerization Assays For Identifying Compounds that Modulate the Expression of a Gene or the Activity of a Gene Product Involved in Diabetes HNF1α forms dimers with itself, as well as with HNF1β. HNF1α dimerizes in the absence of its DNA recognition sequence, therefore, the function of HNF1α can be altered by forming heterodimers with related proteins such as HNF1β. A dimerization co-factor of HNF1α, DCoH (i.e. a factor that enhances dimerization), has been identified (Mendel, D. et al., (1991) *Science* 254:1762–1767).

Recombinant HNF1α and HNF1β genes are expressed and the protein products purified. The purified products are then contacted with a candidate agonist or antagonist in the presence of DCoH. Compounds that stabilize HNF1 homo- and hetero- dimers in the presence of DCoH are antagonists of HNF1.

5.12 Identification of Genes Downstream of HNF1, That are Involved in Insulin Secretion.

In order to identify genes, which are induced by HNF1 and are involved in signaling the cell to secrete insulin, either the wild type or mutant form of HNF1 is transfected into an appropriate cell line, such as a hepatic cell line (e.g. human hepatocellular carcinoma (HepG2)) or a pancreatic beta cell line (e.g. hamster insulinoma (HIT) cells). The transfected cell line is then presented with a glucose challenge in accordance with standard procedures. After various lag times, RNA is isolated from the cells and the different patterns of expression are followed. For example, gene expression induced by a wild type (functional) or mutant HNF1 can be monitored by differential display (Laing, P. and Pardee, A. B. (1992) Science 257:967–971) as further described in example 5.14. Differential display relies on random-primed amplification of a subfraction of total mRNA from two populations. The amplicons (PCR fragments) from the two mRNA populations are run side by side on a sequencing gel. The bands which are expressed at different levels are then isolated and sequenced to identify genes, which are induced by HNF1 and are involved in signaling the cell to secrete insulin.

Alternatively, gene expression can be monitored by representation difference analysis (RDA), another PCR-based technique (Lisitsyn, N. et al. (1993) Science 259:946–951). RDA eliminates fragments present in both populations and detects absolute differences by selective amplification of those RNA fragments that are only found in one population and not the other. These two techniques allow the identification of both novel and known genes.

In addition, to identify known genes that are affected by mutations in the HNF1 gene, RT-PCR combined with Northern analysis can be used. For example,to determine whether novel or known genes identified as described above are directly or indirectly regulated by HNF1, the promoter region of the gene can be sequenced and analyzed to determine whether it contains a sequence homologous to the HNF1 binding site (Tain, J.-M. and Schibler U. (1991) Genes and Development 5:225–2234). Alternatively, gel retardation (Fried, M. and Crothers, D. M. (1981) Nucleic Acids Res. 9:6505–6525) and/or footprinting experiments (Hoess, R. H. and Ambreski, K. (1984) PNAS 81:1026–1029) can be carried out with DNA fragments containing HNF1 binding sites in the presence of purifying wildtype or mutant forms of HNF1 protein.

5.13 Determination of Whether Glucose or a Glucose Metabolite is the Natural Ligand for the HNF4 Steroid Hormone Receptor Exogenously radiolabeled glucose or a glucose metabolite can be added to cells which express HNF4. If the glucose or glucose metabolite is a ligand of HNF4, the binding will result in complex formation and induction of a conformational change resulting in HNF4 homodimerization. The homodimer is then transported to the nucleus where it activates transcription. The HNF4-ligand complex can be precipitated from cells using anti-HNF4 antibodies according to well-known procedures. The ligand can then be identified e.g. via HPLC analysis.

5.14 Identification of Compounds that Modulate the Expression of A Gene or the Activity of a Gene Product Involved in Diabetes Based on the Identification of Genes That Are Differentially Expressed in Tissue From a Diabetic Subject In order to identify differentially expressed genes, RNA, either total or mRNA, may be isolated from one or more tissues (e.g. liver or pancreas) of diabetic subjects. RNA samples are obtained from tissues of experimental subjects and from corresponding tissues of control subjects. Alternatively, RNA may be obtained from the appropriate tissue of transgenic animals that express mutated and wild-type HNF 1. Any RNA isolation technique which does not select against the isolation of mRNA may be utilized for the purification of such RNA samples. See, for example, Sambrook et al., 1989, Molecular Cloning, A Laboratory Manual, Cold Spring Harbor Press, N.Y.; and Ausubel, F. M. et al., eds., 1987–1993, Current Protocols in Molecular Biology, John Wiley & Sons, Inc. New York, both of which are incorporated herein by reference in their entirety. Additionally, large numbers of tissue samples may readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes may be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al., 1984, Nature 308:149–153; Lee, S. W. et al., 1984, Proc. Natl. Acad. Sci. USA 88:2825), and, preferably, differential display (Liang, P., and Pardee, A. B., 1993, U.S. Pat. No. 5,262,311, which is incorporated herein by reference in its entirety), may be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe may correspond to a total cell cDNA probe of a cell type derived from a control subject, while the second cDNA probe may correspond to a total cell cDNA probe of the same cell type derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, e.g., control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing the well known polymerase chain reaction (PCR; the experimental embodiment set forth in Mullis, K. B., 1987, U.S. Pat. No. 4,683,202) which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction may include, but are not limited to, oligo dT-containing primers, preferably of the reverse primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts may be identified those which have been produced from differentially expressed genes.

The reverse oligonucleotide primer of the primer pairs may contain an oligo dT stretch of nucleotides, preferably eleven nucleotides long, at its 5' end, which hybridizes to the poly(A) tail of mRNA or to the complement of a cDNA reverse transcribed from an mRNA poly(A) tail. Second, in order to increase the specificity of the reverse primer, the primer may contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The forward primer may contain a nucleotide sequence expected, statistically, to have the ability to hybridize to cDNA sequences derived from the tissues of interest (e.g. pancreas or liver). The nucleotide sequence may be an arbitrary one, and the length of the forward oligonucleotide primer may range from about 9 to about 13 nucleotides, with about 10 nucleotides being preferred. Arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which may be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis and/or RT-PCR.

Upon corroboration, the differentially expressed genes may be further characterized, and may be identified as target and/or fingerprint genes.

Also, amplified sequences of differentially expressed genes obtained through, for example, differential display may be used to isolate full length clones of the corresponding gene. The full length coding portion of the gene may readily be isolated, without undue experimentation, by molecular biological techniques well known in the art. For example, the isolated differentially expressed amplified fragment may be labeled and used to screen a cDNA library. Alternatively, the labeled fragment may be used to screen a genomic library.

PCR technology may also be utilized to isolate full length cDNA sequences. As described, above, in this Section, the isolated, amplified gene fragments obtained through differential display have 5' terminal ends at some random point within the gene and have 3' terminal ends at a position preferably corresponding to the 3' end of the transcribed portion of the gene. Once nucleotide sequence information from an amplified fragment is obtained, the remainder of the gene (i.e., the 5' end of the gene, when utilizing differential display) may be obtained using, for example, RT-PCR.

In one embodiment of such a procedure for the identification and cloning of full length gene sequences, RNA may be isolated, following standard procedures, from an appropriate tissue or cellular source. A reverse transcription reaction may then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid may then be "tailed" with guanines using a standard terminal transferase reaction, the hybrid may be digested with RNAase H, and second strand synthesis may then be primed with a poly-C primer. Using the two primers, the 5' portion of the gene is amplified using PCR. Sequences obtained may then be isolated and recombined with previously isolated sequences to generate a full-length cDNA of the differentially expressed genes of the invention. For a review of cloning strategies and recombinant DNA techniques, see e.g., Sambrook et al., 1989, supra; and Ausubel et al., 1989, supra.

5.15 Description of an Assay by Which a Hormone Receptor, a Ligand for Such a Receptor or a Protein Having Transcription Activating Properties of a Hormone Receptor can be Detected Generally, the assay involves the use of a cell which contains both DNA encoding a hormone response element (e.g., a promoter) linked to an operative reporter gene, and a DNA encoding a receptor protein. When a suitable hormone or ligand is provided to the cell, a hormone receptor-hormone complex is formed and delivered to an appropriate DNA-binding region to thereby activate the hormone response element and cause expression of the reporter gene. Activation of the reporter gene is detected by standard procedures used for detecting the product of the reporter gene.

Chimeric receptors have been used to localize regions responsible for transcription activation function (Webster et al., Cell 45, 199 (1988). It is thought that a hormone is responsible for allowing a receptor to recognize a DNA response element and the hormone induces a transcription activation function in the hormone-binding domain. The promoter in turn provides an appropriate binding context.

Substituting sequences to recreate the mutant forms can be done, for example, using site directed mutagenesis (Kunkel et al., Methods in Enzymology 154, p. 367 (1987)).

5.16 Cotransfection Assay in HepG2 Cells

Human hepatocellular carcinoma (HepG2) cells are used in a cis-trans assay. Cells are transfected with two DNA transfection vectors. The trans-vector allows efficient production of HNF4, a steroid receptor, in these cells, which do not normally express these receptors. The cis-vector contains an easily assayable gene, in this case the firefly luciferase, coupled to a HNF responsive regulatory sequence. Addition of an HNF4 ligand results in the formation of a ligand receptor complex that activates the luciferase gene, causing light to be emitted from cell extracts. The level of luciferase activity is directly proportional to the effectiveness of the ligand-receptor complex in activating gene expression. This sensitive and reproducible cotransfection approach permits the identification of ligands that interact with an HNF4.

Cells are cultured in DMEM supplemented with 10% charcoal resin-stripped fetal bovine serum, and experiments are conducted in 96-well plates. The plasmids are transiently transfected by the calcium phosphate method (Umesono and Evans, Cell 57:1139–1146 (1989)); Berger et al., J. Steroid Biochem. Molec. Biol. 41:733–738 (1992)) by using 10 ng of a pRS (Rous sarcoma virus promoter) receptor-expression plasmid vector, 50 ng of pRSβ-GAL (β-galactosidase) as an internal control, and 90 ng of carrier plasmid pGEM. Cells are transfected for 6 hours and then washed to remove the precipitate. The cells are then incubated for 36 hours with or without an HNF ligand. After the transfection, all subsequent steps are performed on a Beckman Biomek Automated Workstation. Cell extracts are prepared as described by Berger et al. supra, then assayed for luciferase and β-galactosidase activities. All determinations are performed in triplicate in two independent experiments and are normalized for transfection efficiency by using β-galactosidase as the internal control. Retinoid activity is normalized relative to that of retinoic acid and is expressed as potency (EC50), which is the concentration of retinoid required to produce 50% of the maximal observed response, and efficacy (%), which is the maximal response observed relative to that of retinoic acid at $10^{-5}$M.

6. Deposit of Microorganisms

A BAC clone of genomic DNA containing a mutant HNF1 gene was deposited with the American Type Culture Collection (ATCC) on Nov. 12, 1996 and has been assigned ATCC designation number 97787.

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CATGCTCCTT GGGATGT     17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TGAGGATTGC TTAAAGA     17

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

ATCTCAGTGG TATTTGTGAG C     21

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

TCTGAGTCAC CTGGACAACC     20

( 2 ) INFORMATION FOR SEQ ID NO:5:

( i ) SEQUENCE CHARACTERISTICS:
        ( A ) LENGTH: 36 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CUACUACUAC UAGTGAACTG CACTGTGACA AGCTGC    36

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CUACUACUAC UACACCTGAG GAGTGAATTG GTCG    34

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CTCCAGGCAC TGGGTGAG    18

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CTCCAGCTCT TTGAGGATGG    20

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GCAGATCCCG TCCTTGC    17

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GTCANTACTT ACGCTGCGCC 20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GACGAGGGAA GGTGAGAGTG 20

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CCGTTGTACC TATTGCACTC C 21

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

CAGCCTCAAA CCCTCCG 17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CCAGGGGAGC TGTGAGC 17

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CAGGACACTG CTTCCCTCTC 20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

CTGCTCCAGT ATCTCCCTGC 20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

AGCTGGTGAG TGTCCTTGCT 20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

ACCAGCTTAC CGATGACCAG 20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

ATTAGTGGCA GGTCCCAGTG 20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

ATCCATTGAC AGCCAACCTC 20

( 2 ) INFORMATION FOR SEQ ID NO:21:

( i ) SEQUENCE CHARACTERISTICS:
        ( A ) LENGTH: 20 base pairs ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:21:

TGTAATGGGG AGAGGGTCTG                                                        20

( 2 ) INFORMATION FOR SEQ ID NO:22:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:22:

AGAGCAGCCT CCTGAGCC                                                          18

( 2 ) INFORMATION FOR SEQ ID NO:23:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:23:

CTCCCGCAGA CTATGCTCAT                                                        20

( 2 ) INFORMATION FOR SEQ ID NO:24:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:24:

GCTGCAGGTG CTGGATG                                                           17

( 2 ) INFORMATION FOR SEQ ID NO:25:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:25:

TCCAGCTCCT CTTGTCACCT                                                        20

( 2 ) INFORMATION FOR SEQ ID NO:26:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:26:

TCAGCAGAGC AAGAAAAGCA                           20

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

GCAGATCCCG TCCTTGC                              17

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

GTCANTACTT ACGCTGCGCC                           20

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

AATTAGTATG GTTAATGATC TACAG                     25

( 2 ) INFORMATION FOR SEQ ID NO:30:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

AATTGAACTC TAAGTTCCAC ATCGCCA                   27

---

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method for aiding in the identification of a compound for use in treating Type II diabetes comprising the steps of:
   a) incubating a cell in the presence and absence of a test compound, wherein said cells been altered to contain a nucleic acid molecule comprising an HNF1 response element operably linked to a reporter gene and said cell expresses a wild-type HNF1 protein;
   b) determining the level of expression of said reporter gene in said cell incubated in the presence and absence of said test compound; and
   c) selecting a compound that induces a higher level of expression of said reporter gene in step (b) than that expressed in the absence of said compound, for use in treating Type II diabetes.

2. The method of claim 1, wherein said HNF1 response element is contained in a promoter selected from the group consisting of: liver specific glucokinase, glucose transporter, pyruvate kinase, albumin, aldolase B, UDP-N-acetylglucosamine, an alcohol dehydrogenase, cytochrome P-450, aminopeptidase N, phenylalaninehydroxylase, tyrosine aminotransferase, hepatic triglyceride lipase, apolipoprotein B, apolipoprotein A-II, cholesterol 7 alpha-hydrolase, fibrinogen, alpha-1-microglobulin, C4b-binding protein insulin like growth factor 1 (IGF-1), alpha-fetoprotein, and neural cell adhesion molecule (N-CAM).

3. The method of claim 1, wherein said HNF1 response element is contained in an albumin promoter.

4. The method of claim 1, wherein said cell further expresses a mutant HNF1 protein selected from the group consisting of: an HNF1 protein encoded by a nucleic acid molecule having a base substitution at nucleotide 414 which results in a substitution of an arginine by a tryptophan in the wild-type HNF1 amino acid sequence and an HNF1 protein encoded by a nucleic acid molecule having a nucleotide insertion at nucleotide 895 resulting in a frameshift mutation at residue 895.

5. The method of claim 2, wherein said cell further expresses a mutant HNF1 protein selected from the group consisting of: an HNF1 protein encoded by a nucleic acid molecule having a base substitution at nucleotide 414 which results in a substitution of an arginine by a tryptophan in the wild-type HNF1 amino acid sequence and an HNF1 protein encoded by a nucleic acid molecule having a nucleotide insertion at nucleotide 895 resulting in a frameshift mutation at residue 895.

6. The method of claim 2, wherein said reporter gene is a luciferase gene.

7. The method of claim 3, wherein said reporter gene is a luciferase gene.

8. The method of claim 4, wherein said reporter gene is a luciferase gene.

9. The method of claim 5, wherein said reporter gene is a luciferase gene.

10. A method for identifying a compound for use in treating Type II diabetes comprising the steps of:
   a) incubating a pancreatic cell in the presence and absence of a test compound, wherein said cell has been altered to contain a nucleic acid molecule which encodes HNF1 and said cell produces insulin;
   b) determining the level of insulin expression in said cell incubated in the presence and absence of said test compound; and
   c) selecting a compound that induces a higher level of insulin expression than that expressed in the absence of said compound for use in treating Type II diabetes.

* * * * *

UNITED STATES PATENT AND TRADEMARK OFFICE
CERTIFICATE OF CORRECTION

PATENT NO. : 5,795,726
DATED : August 18, 1998
INVENTOR(S) : M. Alexandra Glucksmann It is certified that error appears in the above-identified patent and that said Letters Patent is hereby corrected as shown below:

On the title page, add the following references:

| OTHER DOCUMENTS | (Including Author, Title, Date, Pertinent Pages, Etc.) |
|---|---|
| Yamagata, et al, "Mutations in the hepatocyte nuclear factor -4α gene in maturity-onset diabetes of the young (MODY1)," Nature, Vol. 384, pp. 458-460 (5 December 1996). | |
| Yamagata, et al, "Mutations in the hepatocyte nuclear factor -1α gene in maturity-onset diabetes of the young (MODY3)," Nature, Vol. 384, pp. 455-458, (5 December 1996). | |

Signed and Sealed this

Sixteenth Day of March, 1999

Attest:

Q. TODD DICKINSON

Attesting Officer      Acting Commissioner of Patents and Trademarks